(12) United States Patent
Nishikawa et al.

(10) Patent No.: US 8,263,004 B2
(45) Date of Patent: Sep. 11, 2012

(54) METHOD AND APPARATUS FOR DEACTIVATING ANTIGENIC SUBSTANCE THROUGH POSITIVE AND NEGATIVE IONS FUNCTIONS

(75) Inventors: Kazuo Nishikawa, Higashiosaka (JP); Hideo Nojima, Nara (JP); Tetsuya Yoneda, Nabari (JP); Kazuhisa Ono, Higashihiroshima (JP); Seiko Shigeta, Hiroshima (JP); Masatoshi Oshita, Fukuchiyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 1027 days.

(21) Appl. No.: 10/545,429

(22) PCT Filed: Feb. 13, 2004

(86) PCT No.: PCT/JP2004/001601
§ 371 (c)(1),
(2), (4) Date: Mar. 19, 2007

(87) PCT Pub. No.: WO2004/073851
PCT Pub. Date: Sep. 2, 2004

(65) Prior Publication Data
US 2007/0199815 A1    Aug. 30, 2007

(30) Foreign Application Priority Data

Feb. 18, 2003  (JP) ................................. 2003-040419
Sep. 1, 2003   (JP) ................................. 2003-309085

(51) Int. Cl.
*A61L 2/00*     (2006.01)
*A61L 101/00*   (2006.01)

(52) U.S. Cl. ... 422/120; 422/121; 422/123; 422/186.04; 361/230; 361/231; 361/233; 204/194

(58) Field of Classification Search ............. 204/403.01, 204/164; 422/186.04, 120, 121, 23; 361/230, 361/231, 233
See application file for complete search history.

(56) References Cited

U.S. PATENT DOCUMENTS

| 7,120,006 B2 * | 10/2006 | Sekoguchi et al. ........... 361/230 |
| 2002/0150540 A1 * | 10/2002 | Yoshikawa et al. ............. 424/43 |
| 2003/0072675 A1 | 4/2003 | Takeda et al. |

FOREIGN PATENT DOCUMENTS

| CA | 2 501 022 A1 | 10/2003 |
| JP | 4-90428 A | 3/1992 |
| JP | 6-154298 A | 6/1994 |
| JP | 07-000807 A | 1/1995 |

(Continued)

OTHER PUBLICATIONS

English Translation of JP 2002-102327; Kohama, Taku; Apr. 9, 2002.*

(Continued)

*Primary Examiner* — Harry D Wilkins, III
*Assistant Examiner* — Zulmariam Mendez
(74) *Attorney, Agent, or Firm* — Birch, Stewart, Kolasch & Birch, LLP

(57) ABSTRACT

The present invention relates to a method of deactivating an antigenic substance by causing positive and negative ions to act on the antigenic substance, and the positive and negative ions are caused to act in an atmosphere in which each of positive ion concentration and negative ion concentration is at least about 50,000/cm$^3$, and more preferably, at least about 100,000/cm$^3$.

**14 Claims, 13

FOREIGN PATENT DOCUMENTS

| | | |
|---|---|---|
| JP | 8-173843 A | 7/1996 |
| JP | 2000-5531 A | 1/2000 |
| JP | 2000-15032 A | 1/2000 |
| JP | 2000-111106 A | 4/2000 |
| JP | 2002-95731 A | 4/2002 |
| JP | 2002-102327 A | 4/2002 |
| JP | 2004-249179 A | 9/2004 |
| JP | 2004-251497 A | 9/2004 |
| JP | 2005-211746 A | 8/2005 |
| JP | 4330351 B2 | 6/2009 |
| WO | WO-03/028880 A1 | 10/2003 |

OTHER PUBLICATIONS

English translation of JP2002-095731; Nishikawa, Kazuo; Apr. 2, 2002.*

English Translation of JP-2002-095731 to Nishikawa Apr. 2, 2002.*

* cited by examiner

METHOD AND APPARATUS FOR DEACTIVATING ANTIGENIC SUBSTANCE THROUGH POSITIVE AND NEGATIVE IONS FUNCTIONS

TECHNICAL FIELD

The present invention relates to method and apparatus for deactivating antigenic substance (also referred to allergen; in the present application, described as antigenic substance) thorough functions of both positive and negative ions. More specifically, the present invention relates to an air conditioning apparatus to which the method and apparatus of present invention is applied (for example, an air purifier, an air conditioner, a dehumidifier, a humidifier, an electric heater, an oil stove, a gas heater, a cooler box and a refrigerator).

BACKGROUND ART

Recently, along with change in residential environment, there has been an increasing demand to remove harmful airborne substance such as pollen and mites causing humane allergic diseases, to realize more healthy and comfortable life. In order to meet such a demand, air conditioning apparatuses with various filters have been developed, as described, for example, in Japanese Patent Laying-Open Nos. 6-154298, 7-807, 8-173843 and 2000-111106.

These air conditioning apparatuses are of the type that absorb or filter harmful airborne substance by sucking in air in the space through a filter. Therefore, such apparatuses inherently necessitate maintenance such as filter exchange for use over a long period of time, and in addition, satisfactory performance can not always be attained because of insufficient properties of the filter.

Though prevention through vaccination has been proposed, it is not always effective, as the amount and quality for immunization differ one person to another.

Therefore, an effective method of suppressing allergic disease without such disadvantage or difficulty has not been known to date.

DISCLOSURE OF THE INVENTION

The present invention was made in view of the foregoing, and its object is to provide effective method and apparatus for suppressing allergic disease that eliminates the trouble of periodic filter exchange or the like and that do not involve any preventive difficulty such as individual difference in antibody development.

Thorough intensive study, the inventors have found that the direct cause of allergic diseases is not the pollen or the like themselves but antigenic substance contained therein, and that deactivation of the antigenic substance is the most effective measure. Based on the findings, the inventors continued study and completed the present invention.

Specifically, the present invention relates to a method of deactivating an antigenic substance by causing positive and negative ions to act against the antigenic substance. The antigenic substance consists of protein or glycoprotein, and when positive and negative ions act on the antigenic substance as such, the substance (particularly the portion reactive to the antibody) is denatured or destroyed. Consequently, allergic reaction is deactivated, and development of allergic disease can be suppressed.

The method of deactivating the antigenic substance can be executed by causing the positive and negative ions to act in an atmosphere in which each of positive ion concentration and negative ion concentration is at least about $50,000/cm^3$. By setting such ion concentration, the antigenic substance can effectively be deactivated, by the function of both positive and negative ions. In the present specification, the ion concentration means concentration of small ions of which critical mobility is at least 1 $cm^2V\cdot sec$. Concentration of small ions was measured using an air ion counter (for example, air ion counter (part number 83-1000B) manufactured by Dan Kagaku).

Further, the method of deactivating the antigenic substance can be executed by causing the positive and negative ions to act in an atmosphere in which each of positive ion concentration and negative ion concentration is at least about $100,000/cm^3$.

Further, the method of deactivating the antigenic substance can be executed by causing the positive and negative ions to act where spatial average concentration of positive ions and spatial average concentration of negative ions are each at least about $3,000/cm^3$. The antigenic substance is diffused and floats in the air, and therefore, it is sometimes more effective to define the concentration in the whole space, rather than the concentration near the outlet port of the apparatus emitting positive and negative ions.

Further, the method of deactivating the antigenic substance can be executed by causing the positive and negative ions to act where spatial average concentration of positive ions and spatial average concentration of negative ions are each at least about $10,000/cm^3$.

In the method described above, the positive ion may be $H_3O^+(H_2O)_n$ (n is 0 or a natural number), and the negative ion may be $O_2^-(H_2O)_m$ (m is 0 or a natural number). Here, $H_3O^+(H_2O)_n$ (n is 0 or a natural number) described as a positive ion can also be described as $H^+(H_2O)_n$ (n is a natural number), and both represent the same ion.

Further, the positive and negative ions may generate, by a chemical reaction, at least one of hydrogen peroxide $H_2O_2$, hydrogen dioxide $HO_2$ and hydroxy radical .OH.

The antigenic substance may be cedar antigenic substance. Alternatively, the antigenic substance may be mite antigenic substance or mite dust.

Further, the present invention relates to a method of deactivating an antigenic substance by denaturing or destroying an antibody-reactive portion of the antigenic substance by electric shock and/or chemical reaction.

According to another aspect, the present invention provides an apparatus for deactivating an antigenic substance, having a mechanism for emitting positive and negative ions to the air, causing the positive and negative ions to act on the antigenic substance.

Further, the apparatus can generate at least one of hydrogen peroxide $H_2O_2$, hydrogen dioxide $HO_2$ and hydroxy radical .OH.

Further, the apparatus can emit positive and negative ions to the air to provide an atmosphere in which each of positive ion concentration and negative ion concentration is at least about $50,000/cm^3$.

Further, the apparatus can emit positive and negative ions to the air to provide an atmosphere in which each of positive ion concentration and negative ion concentration is at least about $100,000/cm^3$.

Further, the apparatus can emit positive and negative ions to the air to attain spatial average concentration of positive ions and spatial average concentration of negative ions each of at least about $3,000/cm^3$.

Further, the apparatus can emit positive and negative ions to the air to attain spatial average concentration of positive ions and spatial average concentration of negative ions each of at least about 10,000/cm$^3$.

In the above-described apparatus, the antigenic substance may be cedar antigenic substance. Alternatively, in the above-described apparatus, the antigenic substance may be mite antigenic substance or mite dust.

Further, the present invention relates to an apparatus for deactivating an antigenic substance, having a discharge mechanism for denaturing or destroying an antibody-reactive portion of the antigenic substance by electric shock and/or chemical reaction.

Each of the above-described apparatuses may have an air conditioning mechanism. Therefore, various air conditioning apparatuses (for example, an air purifier, an air conditioner, a dehumidifier, a humidifier, an electric heater, an oil stove, a gas heater, a cooler box and a refrigerator) capable of deactivating an antigenic substance can be provided.

BEST MODES FOR CARRYING OUT THE INVENTION

<Antigenic Substance>

Figure 1:
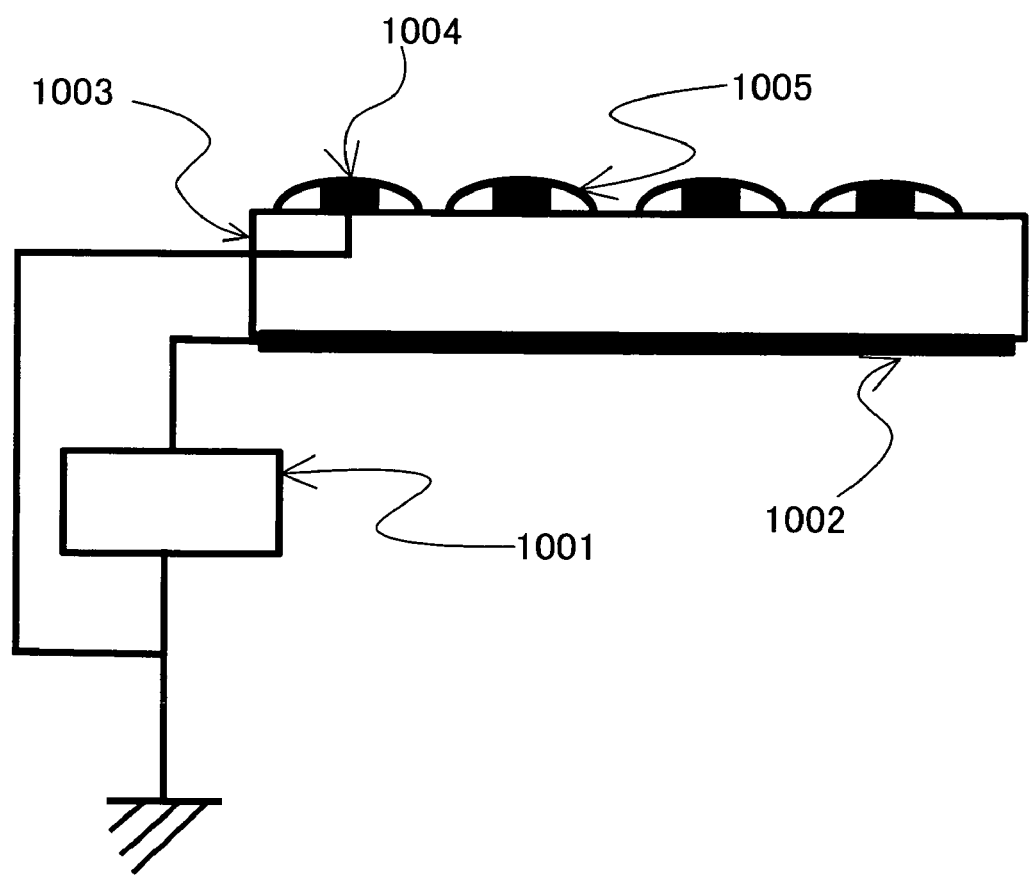
FIG. 1 is a schematic diagram showing an exemplary structure of an ion generating device.

The antigenic substance to be addressed by the present invention refers to a substance included in living organism such as pollen of cedar, cypress or ragweed, or mite, that acts on a living body to cause an allergic reaction as one type of antigen-antibody reaction, inducing allergic disease. Such an antigenic substance typically consists of protein or glycoprotein, and its shape or size is not specifically limited. The protein or glycoprotein itself as molecules, collected particles thereof, or antibody determining radical as a part of the molecular body may be included.

Specific examples of such antigenic substance include cedar antigenic substance and mite antigenic substance.

The mite antigenic substance is included in the body of mite. In general life environment, however, not the antigenic substance in mite itself but in mite dust causes problems. Here, mite dust refers to particles including mite itself, dead mite, part of mite body, mite bait, and body waste of mite. In the present invention, the antigenic substance includes such mite dust.

<Antibody-Reactive Portion>

The antibody-reactive portion refers to a specific portion included in the antigenic substance that combines with the antibody. If the antibody-reactive portion of the antigenic substance were denatured or destroyed (decomposed), the antigenic substance could not combine with the antibody, and therefore, allergic reaction can be suppressed.

<Method of Deactivating Antigenic Substance>

The method of deactivating an antigenic substance in accordance with the present invention is attained by causing positive and negative ions to act against the antigenic substance. As for the positive and negative ions, special effect is not recognized when positive ions only or negative ions only act on the antigenic substance. It is considered that, when both ions exist together, an active substance is generated by a chemical reaction that will be described later, and the active substance attacks protein forming the antigenic substance, particularly the antibody-reactive portion, denaturing or destroying (decomposing) the protein. The antigenic substance is deactivated thereby.

Here, deactivation of an antigenic substance refers to elimination of the antigenic substance by denaturing or destroying (decomposing) the antigenic substance, as well as reduction in amount of the antigenic substance or lowering the activity thereof.

<Concentrations of Both Positive and Negative Ions>

In an atmosphere in which the positive ions and negative ions act on the antigenic substance, the concentration of positive and negative ions is at least 25,000/cm$^3$ each, preferably, 50,000/cm³ and more preferably, 100,000/cm³. When the concentration is smaller than 25,000/cm³, it may be difficult to sufficiently attain the effect on the antigenic substance.

The upper limit of positive and negative ion concentrations is not specifically defined. When ions are generated to an excessively high concentration, a harmful amount of ozone would result, which is not preferable. As will be described later, the positive and negative ions are generated typically by discharge. In order to generate positive and negative ions to a high concentration, application of a high voltage is necessary, and such high voltage may generate ozone as a by-product. In view of this, when concentration of positive and negative ions is set to be not higher than 3,000,000/cm³ each, the ozone concentration at an air blower outlet does not exceed 0.1 ppm, with aging effect considered, when the technique of the present invention is incorporated in a product. The concentration of 0.1 ppm exceeds a reference concentration that is defined as a tolerable concentration for 8-hour work by Japan Society of Occupational Health, and it also exceeds tolerable concentration defined by American Conference of Government Industrial Hygienists (ACGIH). Therefore, the upper limit of the positive/negative ion concentration should be smaller than 3,000,000/cm³, and for higher safety, preferably, smaller than 2,000,000/cm³. Thus, concentration of harmful by-product such as ozone can be made sufficiently lower than the safety limit. Though the example of the upper limit of ion concentration is described above, the limit can be made less strict by improving the method of discharge. The upper limit can similarly be made less strict by providing a structure for decomposing ozone, by arranging a substance that absorbs ozone such as copper oxide or activated carbon. Use of a substance that absorbs ozone only is particularly effective.

As described above, by the method of the present invention, very advantageous effect can be attained that the antigenic substance can be deactivated without generating harmful amount of ozone as a by-product. The atmosphere for deactivating antigenic substance in the present invention refers to an atmosphere in which the concentrations of positive and negative ions are in the above-described range. It is noted that when the above-described ion concentration is attained within 10 cm from a blower outlet of an apparatus emitting positive and negative ions, such a system is considered attaining the atmosphere for deactivating antigenic substance in accordance with the present invention.

In order to deactivate the antigenic substance, spatial average concentration of positive and negative ions should be about at least 3,000/$cm^3$ each, and preferably, at least 10,000/$cm^3$ each. The antigenic substance is diffused and floats in the air, and therefore, it is sometimes more effective to define the concentration in the whole space, rather than the concentration near the outlet of the apparatus emitting positive and negative ions.

Here, if the spatial average concentration of positive and negative ions were smaller than about 3,000/$cm^3$ each, the antigenic substance would not be effectively deactivated. The spatial average concentration of positive and negative ions in the present invention refers to an average concentration in a whole space of a certain volume. This can be measured by measuring concentrations of positive and negative ions at five points apart from each other by at least 50 cm near the center of a room where the air stays appropriately, using an ion counter (for example, ion counter part number ITC-201A, manufactured by Andes Denki), and by calculating an average concentration among the five points.

<Method of Emitting Positive and Negative Ions>

In the present invention, the positive and negative ions are mainly generated by a discharge phenomenon of an ion generating device, and typically, by alternately applying positive and negative voltages, the positive and negative ions can be generated almost simultaneously and emitted to the air. The method of emitting positive and negative ions of the present invention is not limited to this, and it is possible to emit positive or negative ions first by applying either one of positive and negative voltages for a prescribed time period, and to emit ions of the charge opposite to the already emitted ions by applying the other voltage for a prescribed time period. The applied voltage necessary for generating and emitting positive and negative ions may be 2 to 10 kV and preferably 3 to 7 kV as peak-to-peak voltage between electrodes, though it depends on electrode structure.

It is preferred that the positive ions and negative ions of the present invention are generated under relative humidity of 20 to 90%, and preferably 40 to 70%. As will be described later, generation of positive and negative ions is related to existence of water molecules in the air. Specifically, when the relative humidity is smaller than 20%, clustering of water molecule with an ion at the center does not proceed in a satisfactory manner, and re-combination of ions tend to occur, so that the generated ions come to have shorter life. When it exceeds 90%, dews are formed at the surface of the ion generating device, significantly decreasing efficiency of ion generation. Generated ions are too much clustered and surrounded by many water molecules, and because of thus increased weight, ions cannot reach far but undesirably go down. Therefore, ion generation under too low or too high humidity is not preferable.

The method of emitting positive and negative ions of the present invention is not limited to the discharge phenomenon described above, and a method using a device emitting ultraviolet ray or electronic beam may be used.

<Identification of Positive and Negative Ions>

The positive and negative ions of the present invention can be generated using oxygen molecules and/or water molecules existing on a surface of a discharge element as raw material. This method of generation does not require any special raw material, and therefore, it is advantageous in view of cost, and in addition, it is preferred as the raw material is harmless and does not generate any harmful ion or substance.

The composition of positive and negative ions generated by the discharge phenomenon by the ion generating device is as follows. The positive ions are mainly derived from water molecules in the air subjected to electrolytic dissociation by plasma discharge, resulting in hydrogen ions $H^+$, which are clustered with water molecules in the air by solvation energy, to form $H_3O^+(H_2O)_n$ (n is 0 or a natural number). That the water molecules are clustered is clearly understood from the fact that the minimum observed peak appears at a position of molecular weight 19 and that the following peaks successively appear at positions apart by water molecular weight of 18 from this molecular weight 19 in FIG. 2A. This result shows that water molecules having molecular weight of 18 are hydrated to a hydrogen ion $H^+$ having the molecular weight of 1 integrally. As for the negative ions, oxygen molecules or water molecules in the air are subjected to electrolytic dissociation by plasma discharge, generating oxygen ions $O_2^-$, which is clustered with water molecules in the air by solvation energy, to form $O_2^-(H_2O)_m$ (m is 0 or a natural number). That the water molecules are clustered is clearly understood from the fact that the minimum observed peak appears at a position of molecular weight 32 and that the following peaks successively appear at positions apart by water molecular weight of 18 from this molecular weight 32 in FIG. 2B. This result shows that water molecules having molecular weight of 18 are hydrated to an oxygen ion $O_2^-$ having the molecular weight of 32 integrally.

These positive and negative ions emitted to the space surround air-borne antigenic substance, and at the surface of the antigenic substance, the positive and negative ions generate hydrogen peroxide $H_2O_2$, hydrogen dioxide $HO_2$ or hydroxy radical .OH as active spices, through the following chemical reactions (1) and (2).

$$H_3O^++O_2\rightarrow .OH+H_2O_2 \quad (1)$$

$$H_3O^++O_2^-\rightarrow HO_2+H_2O \quad (2)$$

It is understood that hydrogen peroxide $H_2O_2$, hydrogen dioxide $HO_2$ or hydroxy radical .OH generated by the function of positive and negative ions denature or destroy (decompose) the antibody-reactive portion of antigenic substance, making combination between the antigenic substance and the antibody impossible, whereby the antigenic substance in the air can efficiently be deactivated.

In the foregoing, $H_3O^+(H_2O)_n$ (n is 0 or a natural number) has been mainly described as the positive ion and $O_2^-(H_2O)_m$ (m is 0 or a natural number) has been mainly described as the negative ion. The positive and negative ions of the present invention, however, are not limited to these, and $N_2^+$, $O_2^+$ and the like may be included as positive ions and $NO_2^-$ and $CO_2^-$ may be included as negative ions, with the above-described two positive and negative ions being the main component, and similar effects can be expected.

<Ion Generating Device>

The ion generating device of the present invention generates positive and negative ions, and possibly, by the electric shock as will be described later, it can directly deactivate allergic reaction of the antigenic substance. The position of mounting such an ion generating device is not particularly limited. However, generally, it is preferably mounted in an air passage of the apparatus for deactivating antigenic substance. The positive and negative ions generated by the ion generating device disappear in a short period of time, and therefore, the position is determined to efficiently diffuse the positive and negative ions in the air. One, two or more ion generating devices may be mounted.

A conventionally known ion generating device for generating positive and negative ions by a discharge mechanism is used as the ion generating device. Particularly, a device that can emit positive and negative ions to the air to attain the concentration of the positive and negative ions of at least about 50,000/$cm^3$ each in the atmosphere in which the positive and negative ions act against the antigenic substance is preferred. Further, a device that can emit positive and negative ions to the air to attain spatial average concentration of the positive and negative ions of at least about 3,000/$cm^3$ each is preferred.

The discharge mechanism here refers to a mechanism having an insulator sandwiched between electrodes, one of which receives a high AC voltage applied thereto and the other is grounded, and by application of the high voltage, plasma discharge occurs in an air layer in contact with the grounded electrode, causing electrolytic dissociation of water molecules or oxygen molecules in the air to generate positive and negative ions. In such a discharge mechanism, when electrode receiving the high voltage is adapted to have a plate shape or meshed shape and the grounded electrode is adapted to have a meshed shape, electric field concentrates at a mesh end surface of the grounded electrode to cause surface discharge, and a plasma region is formed, when a high voltage is applied. When air is introduced to the plasma region, both positive and negative ions are generated and, besides, electric shock by the plasma is also experienced.

Devices having such a discharging mechanism include, but not limited to, surface discharge device, corona discharge device, plasma discharge device and the like. Further, the shape and material of the electrodes of discharge device are not limited to those described above, and any shape such as a needle shape, and any material may appropriately be selected.

Specifically, an ion generating device having such a structure as shown in FIG. 1 is most preferable, in which a dielectric body 1003 is sandwiched between a plate shaped electrode 1002 and a mesh shaped electrode 1004, positive and negative voltages are alternately applied to the plate-shaped electrode from a power source 1001, whereby electric field concentrates at a mesh end surface of meshed electrode, causing plasma discharge, a plasma region 1005 is formed, and positive and negative ions are generated.

The applied voltage necessary for generating and emitting positive and negative ions may be 2 to 10 kV and preferably 3 to 7 kV as peak-to-peak voltage between electrodes, though it depends on electrode structure.

<Other Methods>

The method of deactivating an antigenic substance is not limited to a chemical reaction, and it can be realized by denaturing or destroying the antibody-reactive portion of the antigenic substance by electric shock. Specifically, the antibody-reactive portion of the antigenic substance is denatured or destroyed also by the plasma discharge itself caused by application of a voltage when the positive and negative ions are generated. Namely, the electric shock can also prevent binding between the antigenic substance and the antibody, whereby the antigenic substance can be deactivated. Therefore, the antigenic substance can be deactivated by denaturing or destroying the antibody-reactive portion of the antigenic substance by electric shock and/or chemical reaction. It is particularly noted that the function described above, that is, synergistic effect of electric shock and chemical reaction, promotes deactivation of antigenic substance.

In the following, the present invention will be described in detail with reference to examples. The present invention, however, is not limited to these embodiments.

Example 1

In the present example, deactivation of antigenic substance by the function of positive and negative ions was confirmed, using cedar pollen as the antigenic substance. Description will be given with reference to FIGS. 3 to 8.

FIG. 3 is a schematic diagram of an apparatus executing a method of deactivating antigenic substance by the function of positive ions and negative ions. FIGS. 4A, 4B, 5A and 5B represent reactivity evaluation of cedar antigenic substance (simply referred to as CJP) and serum IgE of a total of 42 patients 19 to 60, in accordance with ELISA method. The apparatus shown in FIG. 3 includes the ion generating device shown in FIG. 1, and FIGS. 2A and 2B show mass spectra of positive and negative ions emitted therefrom.

<Apparatus for Executing the Method of Deactivating Antigenic Substance>

First, in the apparatus shown in FIG. 3, a surface discharge device having a flat shape of 37 mm length and 15 mm width was used as an ion generating device 1021 (same as the ion generating device shown in FIG. 1). By alternately applying positive and negative voltages between the electrodes, surface discharge is caused at a surface electrode portion, and by discharge plasma in atmospheric pressure, positive ions 1022 and negative ions 1023 are almost simultaneously generated and emitted. The applied voltage was 3.3 kV to 3.7 kV in terms of peak-to-peak voltage between the electrodes, and with the voltage in this range, harmful amount of ozone was not generated. Four such ion generating devices were mounted and fixed on a cylindrical sealed container 1027 formed of acryl and having an inner diameter of 140 mm and the length of 500 mm. On one side of the container, an inlet 1028 for spraying a solution containing the antigenic substance is provided, on another side, a recovery vessel 1025 for recovering the solution containing the antigenic substance is provided, and in addition, at the bottom of the container, exhaustion outlet 1026 for deaeration is provided.

Figure 3:
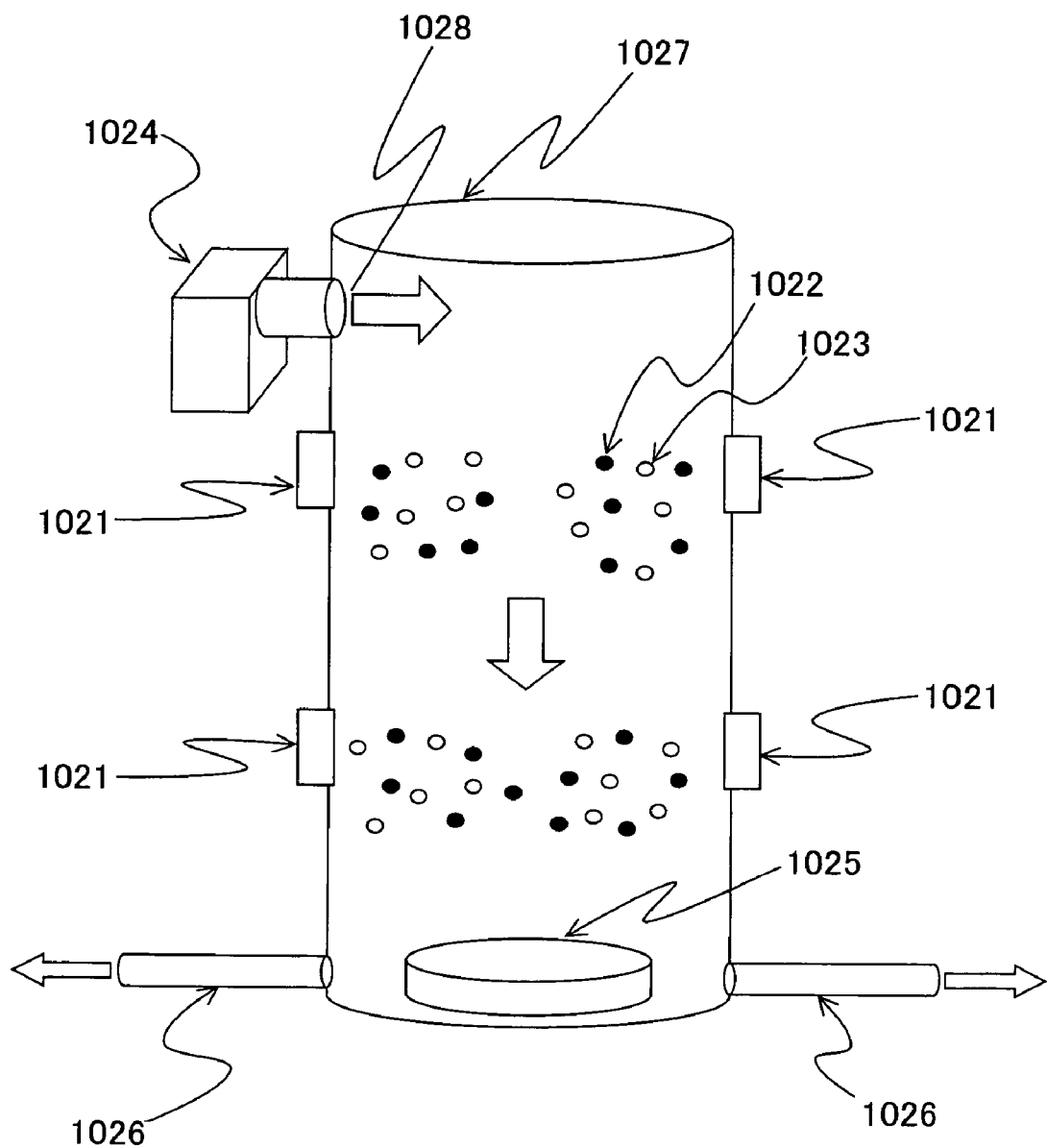
FIG. 3 is a schematic diagram showing an example of an apparatus for executing the method of deactivating the antigenic substance.
Figure 4A:
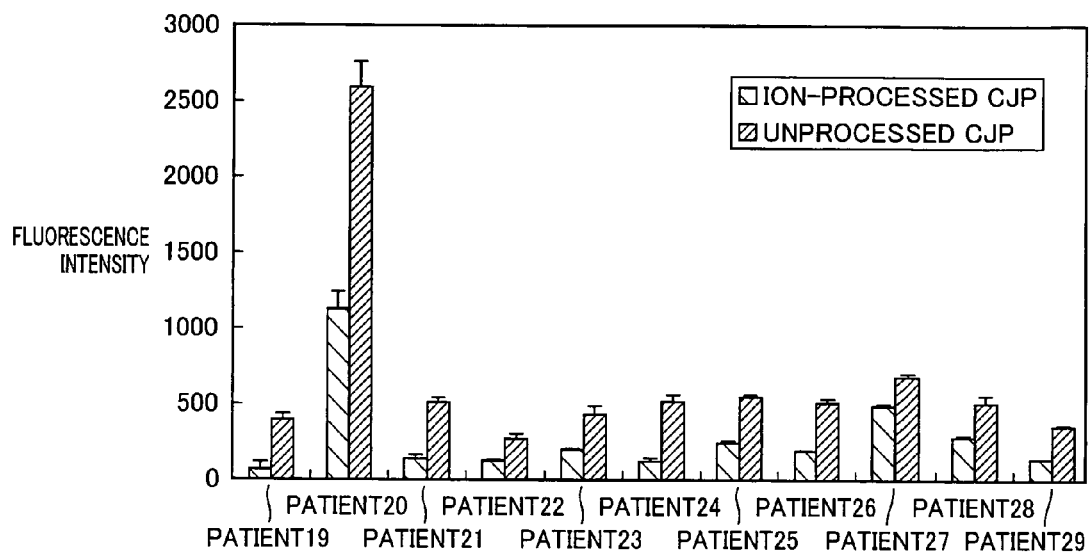
FIG. 4A represents relation of allergic reaction of serum IgE antibody and ion-processed and unprocessed antigenic substances (cedar antigenic substance) of hay fever patients 19 to 29.
Figure 4B:
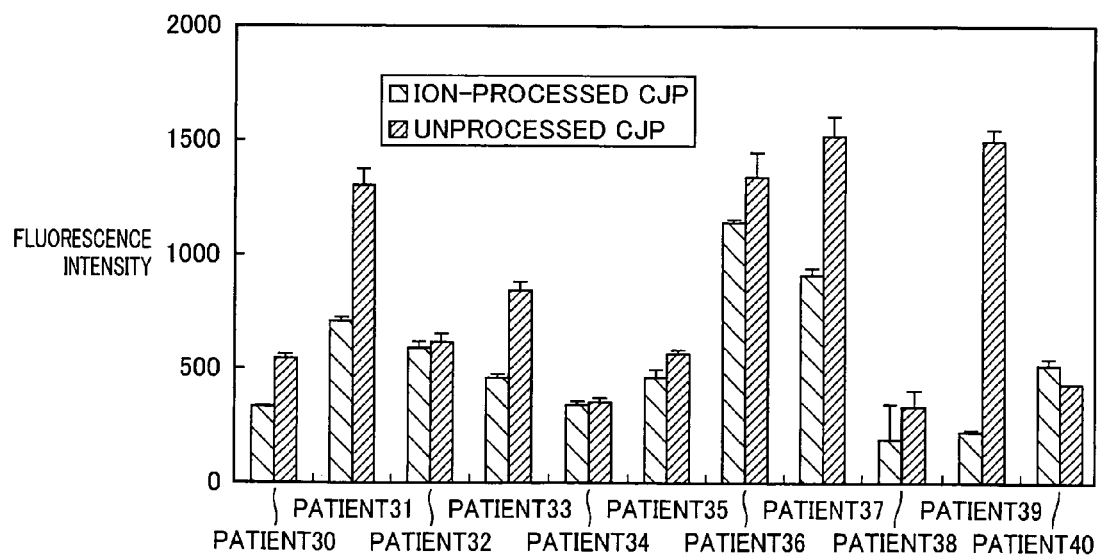
FIG. 4B represents relation of allergic reaction of serum IgE antibody and ion-processed and unprocessed antigenic substances (cedar antigenic substance) of hay fever patients 30 to 40.
Figure 5A:
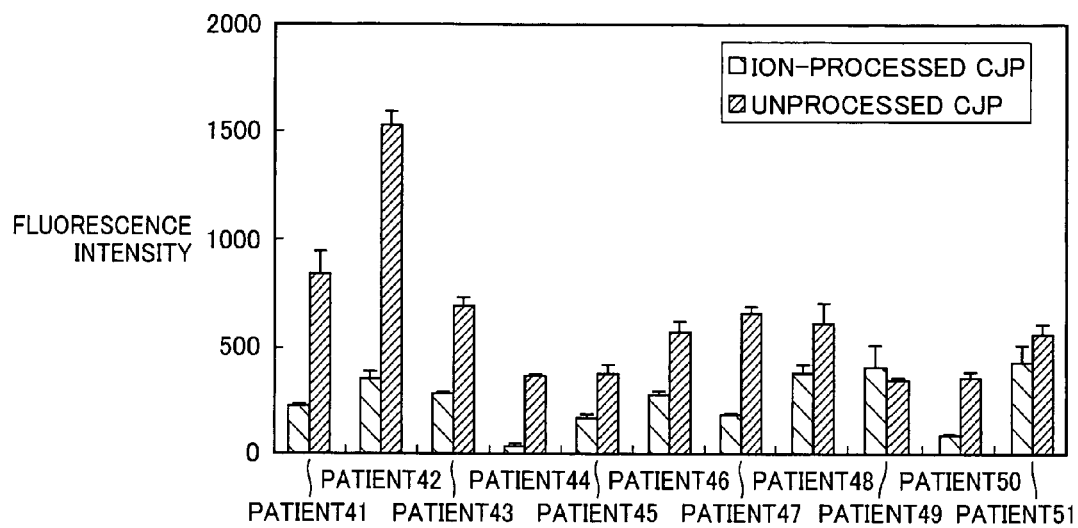
FIG. 5A represents relation of allergic reaction of serum IgE antibody and ion-processed and unprocessed antigenic substances (cedar antigenic substance) of hay fever patients 41 to 51.
Figure 5B:
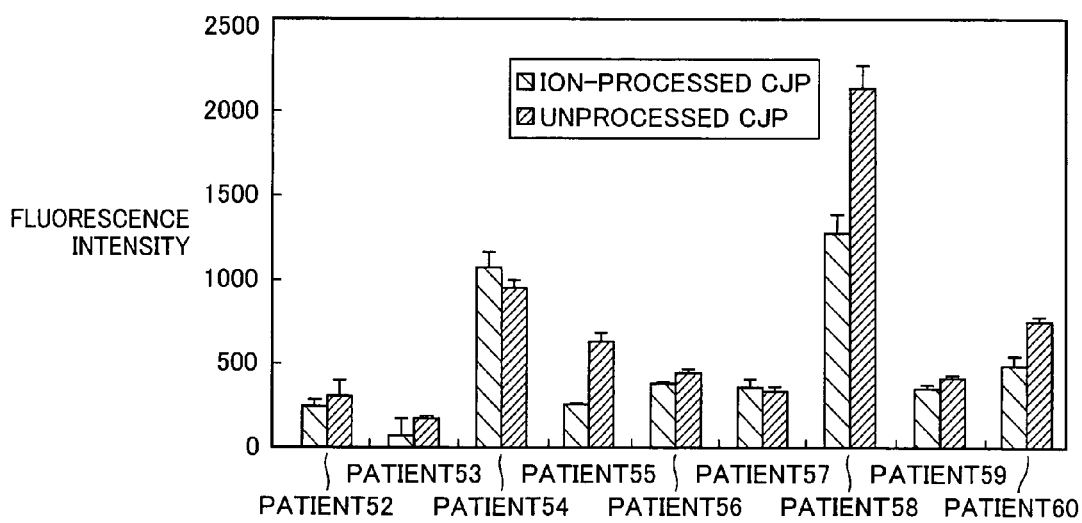
FIG. 5B represents relation of allergic reaction of serum IgE antibody and ion-processed and unprocessed antigenic substances (cedar antigenic substance) of hay fever patients 52 to 60.
Figure 6:
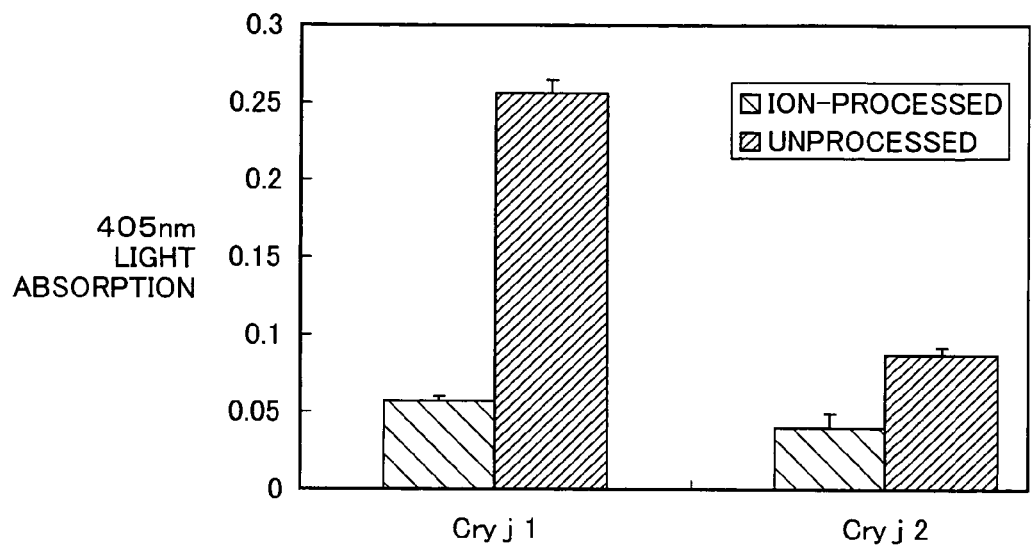
FIG. 6 represents relation of reactivity between Cry j 1 and Cry j 2 and monoclonal antibody, with ion-processed and unprocessed antigenic substances.
Figure 7:
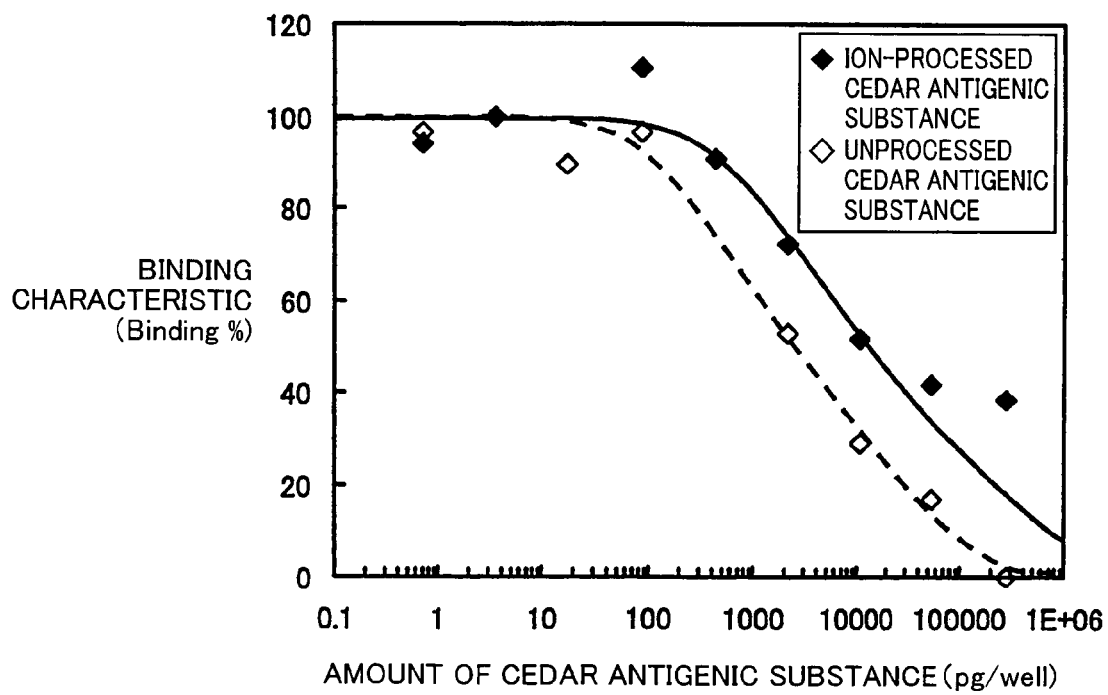
FIG. 7 represents relation of allergic reaction between the antigenic substance and the serum IgE antibody of hey fever patients, when the antigenic substance (cedar antigenic substance) were ion-processed and unprocessed, by ELISA inhibition method.

Specifically, in the apparatus shown in FIG. 3, the antigenic substance is sprayed through inlet 1028 and naturally falls to the recovery vessel 1025, while the substance is exposed to positive and negative ions and reacts therewith.

<Cedar Pollen and Antigenic Substance>

As the antigenic substance, substance extracted from cedar pollen was used. The cedar pollen was collected from branches of Japanese cedar (scientific name: *Cryptomeria japonica*) grown in Yutakamachi, Hiroshima prefecture. The pollen was collected using a vacuum cleaner with a mesh, and then sifted. After collection, the pollen was stored in a freezer at $-30°$ C.

In order to extract the antigenic substance from the cedar pollen, 80 g of cedar pollen was stirred in 3.2 L of 20 mM phosphate buffer solution (PBS, pH7.4) at 4° C. for 4 hours, and thereafter subjected to centrifugal separation for 30 minutes at 6000 rpm. Thereafter, ammonium sulfate was added to the supernatant to attain final saturated concentration of 80%, and centrifugal separation was performed for 30 minutes at 6000 rpm. After centrifugal separation, dialysis with the duration of 6 hours was repeated 6 times, and centrifugal separation was performed for 30 minutes at 10,000 rpm. After the centrifugal separation, the resulting supernatant was freeze-dried, as the cedar antigenic substance. It is noted that the cedar antigenic substance includes Cry j 1 and Cry j 2, as antigenic substances.

<Protein Determination by Folin-Lowry Method>

A solution containing the cedar antigenic substance 0.2 ml was mixed with 1 ml of solution D, as specified below, and left for 10 minutes. Then, 0.1 ml of solution A, as specified below, was added and left for 30 minutes, and light absorption at 750 nm was measured. Further, a standard series was formed with bovine serum albumin (BSA) to form a working curve, whereby the amount of protein in the cedar antigenic substance was determined as BSA equivalent. As a result, protein concentration was 200 ng/ml. Reagents used here are as follows.

(Reagents)
Solution A; 1N of phenol reagent, as acid.
Solution B; 2% of $Na_2CO_3$+0.1 N of NaOH
Solution C; 0.5% of $CuSO_4.5H_2O$+1% of sodium citrate
Solution D; Solution B: Solution C=50:1 (v/v)

<Spraying and Recovery of Antigenic Substance>

The solution containing cedar antigenic substance as the antigenic substance obtained in this manner (protein concentration 200 ng/ml) of 8 ml was put in a nebulizer 1024, which was connected to inlet 1028 for spraying antigenic substance solution of the apparatus shown in FIG. 3. In order to recover the sprayed solution containing antigenic substance, recovery vessel 1025 was placed at the bottom of cylindrical sealed container 1027.

The nebulizer was connected to an air compressor and sprayed the antigenic substance through inlet 1028, using compressed air (flow rate 5 L/min). The amount sprayed was 8.0 ml (duration: 90 min). After 90 minutes, the antigenic substance sedimented at the bottom of cylindrical sealed container 1027 was recovered by recovery vessel 1025. It took about 90 seconds for the sprayed antigenic substance to naturally fall through cylindrical sealed container 1027.

Such spraying and recovery of antigenic substance was performed twice, with the ion generating device 1021 in operation (that is, with ion-processing) and not in operation (that is, without ion-processing).

Figure 2A:
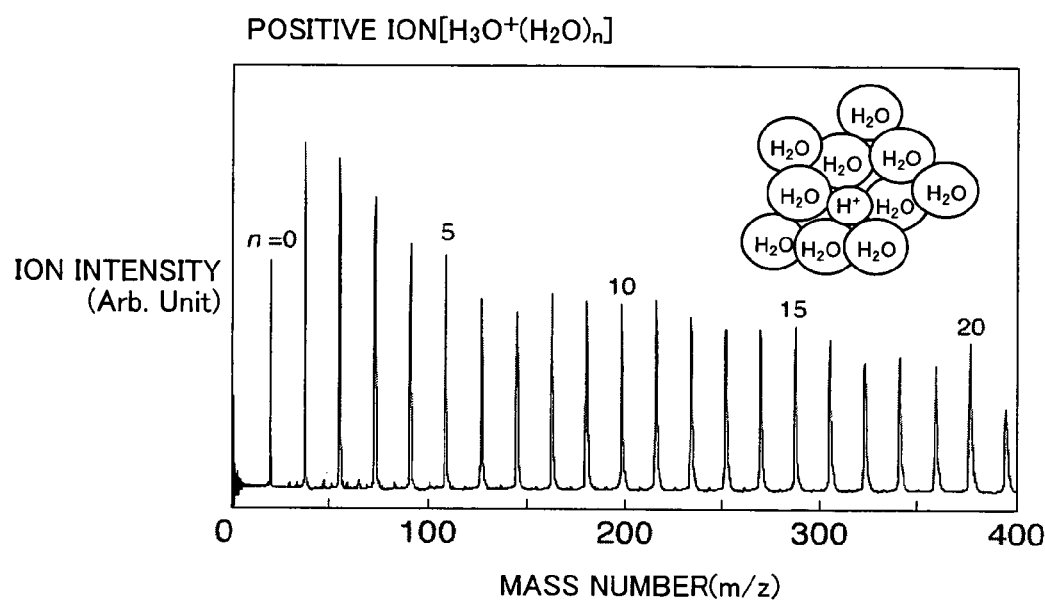
FIG. 2A represents mass spectrum of positive ions generated from the ion generating device.
Figure 2B:
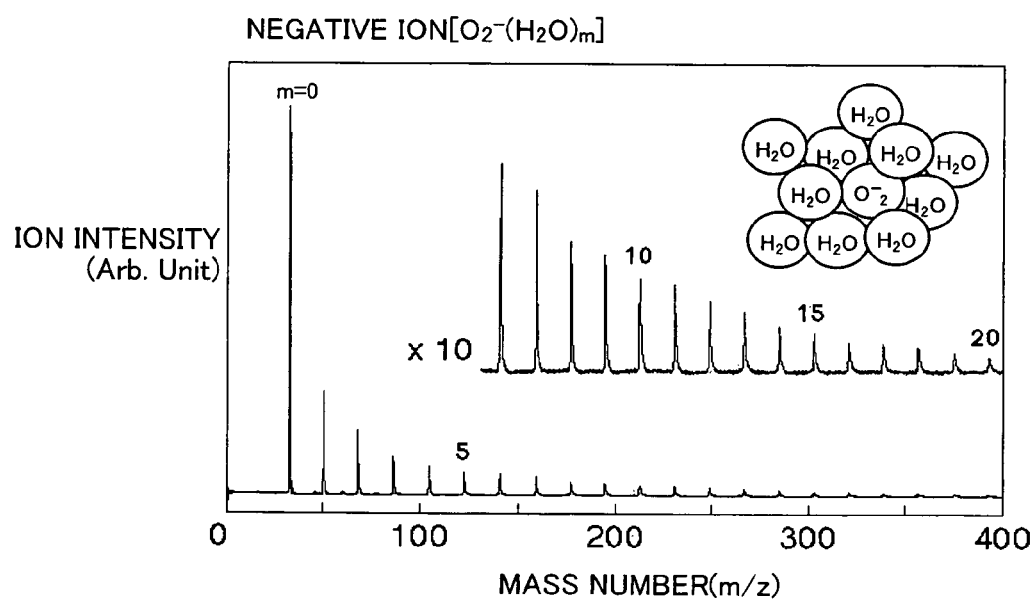
FIG. 2B represents mass spectrum of negative ions generated from the ion generating device.

When ion generating device 1021 was operated so that positive and negative ions reacted against the antigenic substance, the concentrations of positive and negative ions in the atmosphere (in cylindrical sealed container 1027) were measured by introducing air at the flow rate of 5 L/min by an air compressor through inlet 1028 of cylindrical sealed container 1027 for spraying antigenic substance solution with ion generating devices mounted, and by placing air ion counter (part number 83-1001B) manufactured by Dan Kagaku at recovery vessel 1025 for recovering the antigenic substance solution, measuring the positive and negative ion concentrations. As a result, when voltage of 3.3 kV to 3.7 kV as the peak-to-peak voltage between electrodes was applied to ion generating devices 1021, the concentrations of positive and negative ions were each $100,000/cm^3$, in the cylindrical sealed container 1027. The atmosphere in the space had the temperature of 25° C. and relative humidity of 60% RH. As shown in FIGS. 2A and 2B, respectively, it was considered that the emitted positive ions were $H_3O^+$ $(H_2O)_n$ (n is 0 or a natural number) and negative ions were $O_2^-$ $(H_2O)_m$ (m is 0 or a natural number), and that these positive and negative ions generate hydrogen peroxide $H_2O_2$, hydrogen dioxide $HO_2$ or hydroxy radical .OH by the chemical reactions (1) and (2) described above.

<Reactivity Evaluation by ELISA Method>

Next, reactivity between the cedar antigenic substance collected in this manner and the serum IgE antibody taken from hey fever patients 19 to 60 was measured by ELISA (enzyme-liked immunosorbent assay) method. As for the antigenic substance, those reacted with positive and negative ions (ion-processed cedar antigenic substance) and not reacted (un-processed cedar antigenic substance) were compared to evaluate the reactivity.

Specifically, using a 96-well plate for ELISA, ion-processed cedar antigenic substance and unprocessed cedar antigenic substance diluted to 0.1 μg/ml with bicarbonate buffer solution were applied, 50 μl per well. At the same time, human IgE standard double-diluted five times from 200 μg/ml with bicarbonate buffer solution was applied, 50 μl per well, and left still for 2 hours at a room temperature. The plate was washed three times with washing buffer, and a blocking buffer of 300 μl was applied and left still overnight at 4° C.

After left still for one night, the plate washed three times, serum of cedar hey fever patient diluted ten times with (3% of skim milk+1% of BSA)/PBST and incubated for one hour was applied, 50 μl per well, and left still for 4 hours. The plate washed three times, and biotin-labeled anti-human IgE diluted 1000 times with (3% of skim milk+1% of BSA)/PBST was applied, 50 μl per well, and left still for 2.5 hours.

After left still, the plate washed three times, 50 μl of alkali phosphatase labeled streptavidin diluted 1000 times with (3% of skim milk+1% of BSA)/PBST was applied, and left still for 1.5 hours at a room temperature. The plate washed four times, Attophos™ substrate buffer was applied, 50 μl per well, and left until colored, with light shielded. Fluorescent intensity was measured using a spectrophotometer (Cyto™ Fluor II). Results are as shown in FIGS. 4A, 4B, 5A and 5B.

As shown in FIGS. 4A, 4B, 5A and 5B, reactivity (binding characteristic) between serum IgE antibody of hey fever patients and cedar antigenic substance where the ion generating device 1021 was not operated (that is, positive and negative ions were not generated and ion-processing does not occur) and where concentrations of positive and negative ions were both 100,000/cm$^3$ was confirmed. Among 42 patients (#19 to #60), 38 patients exhibited significant decrease in reactivity between the ion-processed antigen and the serum IgE antibody of the patients (lower fluorescence intensity represents lower reactivity), except for patients #40, #49, #54 and #57. Among these patients, 33 exhibited remarkably decreased antibody reactivity. Reagents used here are as follows.

(Reagents)
Sodium hydrogen carbonate buffer (bicarbonate buffer) solution; 100 mM of $NaHCO_3$ (pH 9.2~9.5)

Phosphate buffer solution (PBS); 4 g of NaCl, 0.1 g of $Na_2HPO_4.12H_2O$, 1.45 g of KCl, 1 g of $KH_2PO_4$, mixed with distilled water to 500 ml PBST; PBS+0.5% of Tween-20

Blocking buffer solution; PBS+3% of skim milk+1% of BSA

Washing buffer solution; 43 g of $Na_2HPO_4.12H_2O$, 3.6 g of $NaH_2PO_4$, 263 g of NaCl, 15 ml of Tween-20, mixed with distilled water to 3 L.

<Reactivity Evaluation with Monoclonal Antibody by ELIZA Method>

Decrease in reactivity between antigenic substances Cry j1 and Cry j 2 with monoclonal antibody was studied, where ion generating device 1021 was not operated and where a voltage of 3.3 kV to 3.7 kV was applied as peak-to-peak voltage between electrodes of the device to emit positive and negative ions to attain concentration of 100,000/$cm^3$ for each of positive and negative ions in cylindrical sealed container 1027 after spraying by nebulizer 1024.

Specifically, using a 96-well plate for ELISA, ion-processed Cry j 1, ion-processed Cry j 2, unprocessed Cry j1 and unprocessed Cry j 2 diluted to 0.1 μg/ml with bicarbonate buffer solution was applied, 50 μl per well. The plate washed three times with washing buffer solution, and then 300 μl of blocking buffer solution was applied, and left still overnight at 4° C.

After left still for one night, the plate washed three times, Cry j 1 and Cry j 2 rabbit antibody diluted 1000 times with (3% of skim milk+1% of BSA)/PBST was applied, 50 μl per well, and left still for one hour. Thereafter, the plate washed three times, and 50 μl of HRP labeled anti-rabbit IgE diluted 1,500 times with (3% of skim milk+1% of BSA)/PBST was applied to the well, and left still for one hour.

After left still, the plate washed three times, 50 μl of substrate solution (consisting of 500 μl of ABST (20 mg/ml), 10 μl of 30% hydrogen peroxide solution, 1 ml of 0.1M citric acid (pH 4.2) and 8.49 ml of distilled water) was applied to the well, and left still until colored, with the light shielded. Fluorescent intensity was measured using a spectrophotometer (ARVO™ SX). The reagents used were the same as those listed above, unless specified differently.

The results obtained by the process above are as shown in FIG. 6. Referring to FIG. 6, when we compare the result where the ion generating device was not operated (that is, unprocessed Cry j1 and unprocessed Cry j 2) and the result where the device was operated to attain an atmosphere having positive and negative ion concentrations of 100,000/$cm^3$ each (that is, ion-processed Cry j1 and ion-processed Cry j 2), it could be confirmed that reactivity (binding characteristic) between ion-processed Cry j 1 and Cry j 2 as the antigenic substances and the monoclonal antibody was significantly decreased. Specifically, reactivity between Cry j 1 and monoclonal antibody was decreased to about one fifth before and after ionization, and decreased to about one half in the case of Cry j 2.

<Evaluation by ELIZA Inhibition Method>

For quantitative evaluation of reactivity between ion-processed and unprocessed cedar antigenic substances and serum IgE of hey fever patients, ELIZA inhibition (enzyme-liked immunosorbent assay inhibition) method was used.

Specifically, the cedar antigenic substance recovered after spraying was put in a centrifugal separator (Centriprep YM-10), and subjected to centrifugal condensation at 2500 rpm. Further, the condensation was put in a centrifugal separator (ULTRA FLEE-MC) and subjected to centrifugal condensation at 7000 rpm. Condensed ion-processed cedar antigenic substance and condensed unprocessed cedar antigenic substance were 5-times diluted from protein concentration of 11 μg/ml for 8 times. The diluted antigenic substances, 50 μl each, were mixed with 50 μl of 10-times diluted serum IgE of each patient, and pre-incubated overnight at 4° C.

Specifically, using a 96-well plate for ELISA, 50 μl of cedar antigenic substance (not even sprayed) diluted to 1 μg/ml with bicarbonate buffer solution was applied to a well, and left still for 2 hours. The plate washed three times with washing buffer solution, and then, 300 μl of blocking buffer solution was applied and left still overnight at 4° C.

After left still overnight, the plate washed three times, and pre-incubated samples were applied, 50 μl per well, and left still for 4 hours. The plate washed three times, and biotin-labeled anti-human IgE diluted 1000 times with (3% of skim milk+1% of BSA)/PBST was applied, 50 μl per well, and left still for 2.5 hours.

After left still, the plate washed three times, 50 μl of alkali phosphatase labeled streptavidin diluted 1000 times with (3% of skim milk+1% of BSA)/PBST was applied, and left still for 1.5 hours at a room temperature. The plate washed four times, Attophos™ substrate buffer was applied, 50 μl per well, and left until colored, with light shielded. Fluorescent intensity was measured using a spectrophotometer (Cyto™ FluorII). The reagents used were the same as those listed above, unless specified differently.

Reactivity (binding characteristic) to the serum IgE antibody of hey fever patients, where ion generating device was not operated (that is, reactivity to unprocessed cedar antigenic substance) and where a voltage of 3.3 kV to 3.7 kV was applied as peak-to-peak voltage between electrodes of the device to emit positive and negative ions to attain concentration of 100,000/$cm^3$ of positive and negative ions each in cylindrical sealed container 1027 (that is, reactivity to ion-processed cedar antigenic substance) was studied. The results are as shown in FIG. 7.

As shown in FIG. 7, the amount of cedar antigenic substance necessary for 50% inhibition (to lower reactivity of cedar antigenic substance to serum IgE antibody to 50%) was $2.53\times10^3$ pg/well in the case of cedar antigenic substance not subjected to ion-processing, while the necessary amount for 50% inhibition was $1.34\times10^4$ pg/well in the case of ion-processed cedar antigenic substance, and therefore, the ratio of deactivation was confirmed to be 81%. Here, the ratio of deactivation was calculated in accordance with the equation (1).

$$\text{Ratio of deactivation }\% = (1-A/B)\times100 \qquad (1)$$

A: amount of unprocessed cedar antigenic substance necessary for 50% inhibition

B: amount of ion-processed cedar antigenic substance necessary for 50% inhibition <Relation Between Positive/Negative Ion Concentration and Ratio of Deactivation>

Using the serum IgE of patient #19 subjected to the ELIZA method above as an antibody, fluorescence intensity of unprocessed cedar antigenic substance and ion-processed cedar antigenic substance were found by the ELIZA method in the similar manner as described above (specifically, the apparatus of FIG. 3 was used, and for ion-processing, concentration of 100,000/cm$^3$ was attained both for positive and negative ions), with four different concentrations (in terms of protein concentrations) of the antigenic substance (cedar antigenic substance) of 100 ng/ml, 200 ng/ml, 400 ng/ml and 800 ng/ml. From the fluorescence intensity, ratio of deactivation of allergic reaction was calculated in accordance with the equation (2). The results are as shown in Table 1 below.

TABLE 1

|  | Concentration of antigenic substance (ng/ml) | | | |
| --- | --- | --- | --- | --- |
|  | 100 | 200 | 400 | 800 |
| Ratio of deactivation (%) | 94 | 83 | 78 | 56 |

$$\text{Ratio of deactivation \%} = (1 - C/D) \times 100 \quad (2)$$

C: Fluorescence intensity of ion-processed cedar antigenic substance

D: Fluorescence intensity of unprocessed cedar antigenic substance

Thereafter, selecting the sample having the antigenic substance concentration of 200 ng/ml as a reference, assuming that the following relation holds between the ion concentration and the concentration of the antigenic substance, relation between the positive and negative ion concentrations and the ratio of deactivation was calculated. Specifically, if the ratio of deactivation were constant, there would be a prescribed relation held between the ion concentration and the concentration of the antigenic substance concentration. For example, when the ion concentration is kept constant and the concentration of the antigenic substance is decreased to one half and when the concentration of the antigenic substance is kept constant and the ion concentration was doubled, it follows that the same ratio of deactivation results. Therefore, using the two points that the ion concentrations of positive and negative ions are each 100,000/cm$^3$ and that the concentration of the antigenic substance is 200 ng/ml as references, the relation between the positive and negative ion concentrations and the ratio of deactivation is plotted in FIG. 8. Specifically, the data obtained when the positive/negative ion concentrations were 25,000/cm$^3$, 50,000/cm$^3$, 100,000/cm$^3$ and 200,000/cm$^3$ correspond to the data obtained when the concentrations of the antigenic substance in accordance with ELIZA method described above were 800 ng/ml, 400 ng/ml, 200 ng/ml and 10 ng/ml, respectively (in FIG. 8, the abscissa represents each of positive and negative ion concentrations).

Figure 8:
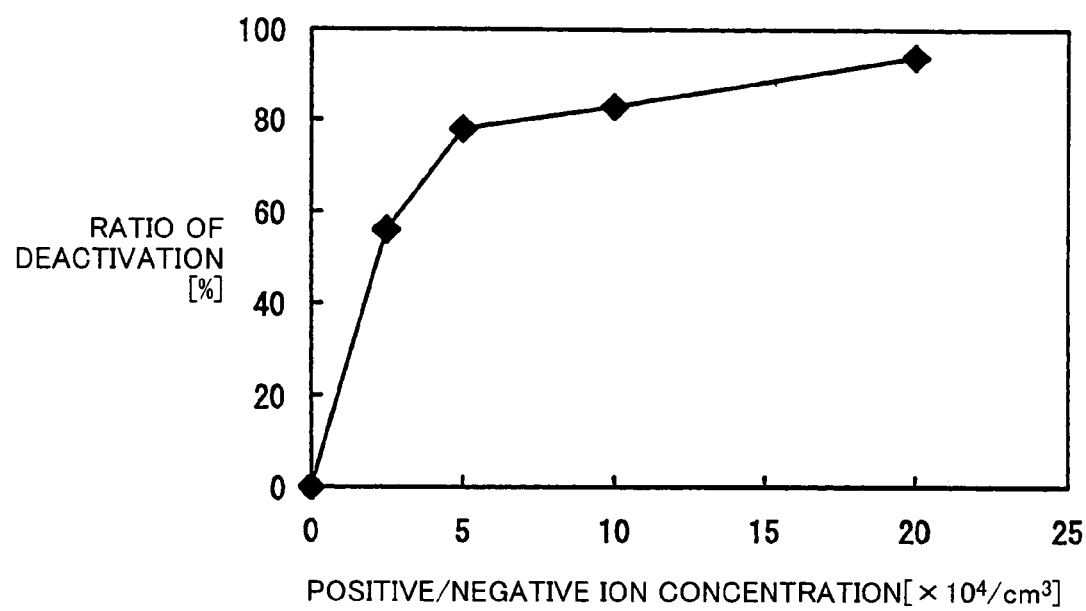
FIG. 8 represents relation between concentrations of positive/negative ions and ratio of deactivation.

As is apparent from FIG. 8, when the positive/negative ion concentration increases, the ratio of deactivation also increases, and when each of the positive and negative ion concentrations is 50,000/cm$^3$, reaction deactivation as high as about 78% can be attained, realizing stable effect of deactivating antigenic substance. When each of the positive and negative ion concentrations is 100,000/cm$^3$, reaction deactivation as high as about 83% can be attained, and when each of the positive and negative ion concentrations is 150,000/cm$^3$, reaction deactivation as high as about 90% can be attained, so that it becomes possible to effectively suppress allergic disease such as hey fever or mite allergy.

<Intradermal Test>

Each of ion-processed cedar antigenic substance and unprocessed cedar antigenic substance was diluted to protein concentration of 0.5 μg/ml with 0.9% of NaCl, and 0.02 ml of the resulting sample was injected to cedar hey fever patients on their inner forearm, using a syringe for tuberculin test. After about 15 minutes, longer and shorter diameters of appeared erythema and wheal were measured, and reactivity was evaluated from the average diameter. The results are as shown in Table 2.

TABLE 2

|  | Intradermal Reaction Test | | Conjunctival Reaction Test | |
| --- | --- | --- | --- | --- |
| Patient | Unprocessed | Ion-processed | Unprocessed | Ion-processed |
| A | +++ | + | − | − |
| B | +++ | + | + | − |
| C | +++ | + | + | − |
| D | +++ | + | + | − |
| E | +++ | + | + | − |
| F | +++ | + | + | − |

In Table 2 above, "−" denotes that reddish area or erythema is smaller than 10 mm, "±" denotes reddish area of 10 mm to 20 mm, "+" denotes reddish area of 20 mm to 30 mm or swelling or wheal of 10 mm or smaller, "++" denotes reddish area of 30 mm to 40 mm or swelling of 10 mm to 15 mm, and "+++" denotes reddish area of 40 mm or larger or swelling of 15 mm or larger with pseudopod.

As can be seen from Table 2, when the unprocessed case where the ion generating device was not operated (that is, positive and negative ions are not generated, unprocessed cedar antigenic substance) and the case where processing is done in an atmosphere having positive and negative ion concentrations of 100,000/cm$^3$ each (ion-processed cedar antigenic substance) were compared, it could be confirmed that all six patients A to F had the intradermal reaction soothed significantly.

<Conjunctival Reaction Test>

Ion-processed cedar antigenic substance and unprocessed cedar antigenic substance were diluted to protein concentration of 5 μg/ml with 0.9% of NaCl, and 5 μl of the resulting sample was dripped to the eyes of cedar hey fever patients A to F using a pipet. After about 15 minutes, conjunctival reactions appeared as congestion of plica semilunaris, lid and bulbar conjuctiva, itch, lacrimation and the like were observed.

The determination is as follows: "−" denotes no congestion, "±" denotes slight congestion and itching, "+" denotes congestion either at an upper or lower portion of the conjunctiva, "++" denotes congestion both at upper and lower portions of the conjunctiva, "+++" denotes congestion entirely over the conjunctiva, and "++++" denotes eyelid edema and the like. The results are also shown in Table 2.

As shown in Table 2, when the unprocessed case where the ion generating device was not operated (that is, positive and negative ions are not generated, unprocessed cedar antigenic substance) and the case where processing is done in an atmosphere having positive and negative ion concentrations of 100,000/cm$^3$ each (ion-processed cedar antigenic substance) were compared, it could be confirmed that among six hey fever patients A to F, five patients except for patient A had the conjectival reaction soothed significantly.

Example 2

In this example, deactivation of antigenic substance by the function of positive and negative ions was confirmed, using mite dust antigenic substance. Description will be given in the following with reference to FIGS. 9 and 10.

Figure 9:
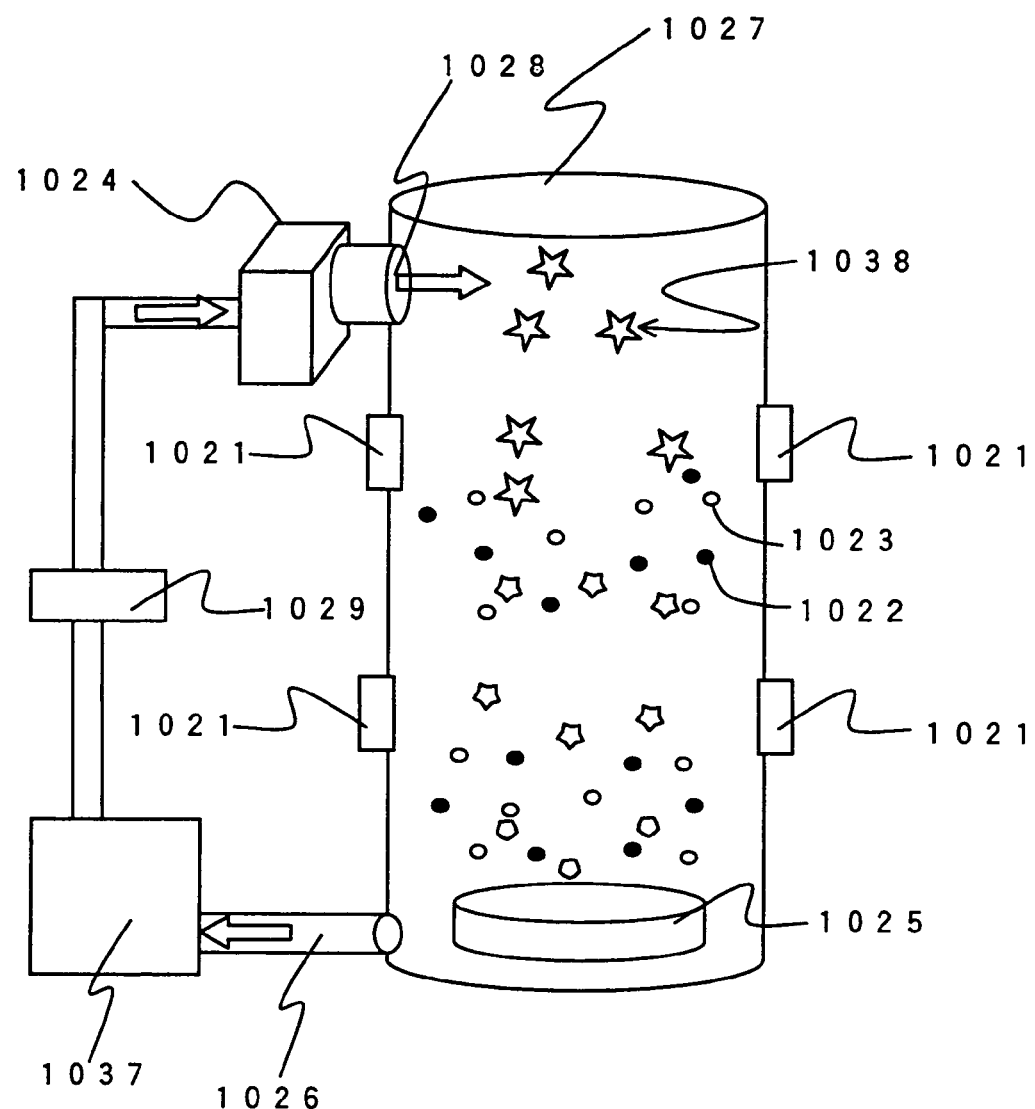
FIG. 9 is a schematic diagram showing an apparatus for executing the method of deactivating antigenic substance, having a mechanism for decreasing ozone concentration.
Figure 10:
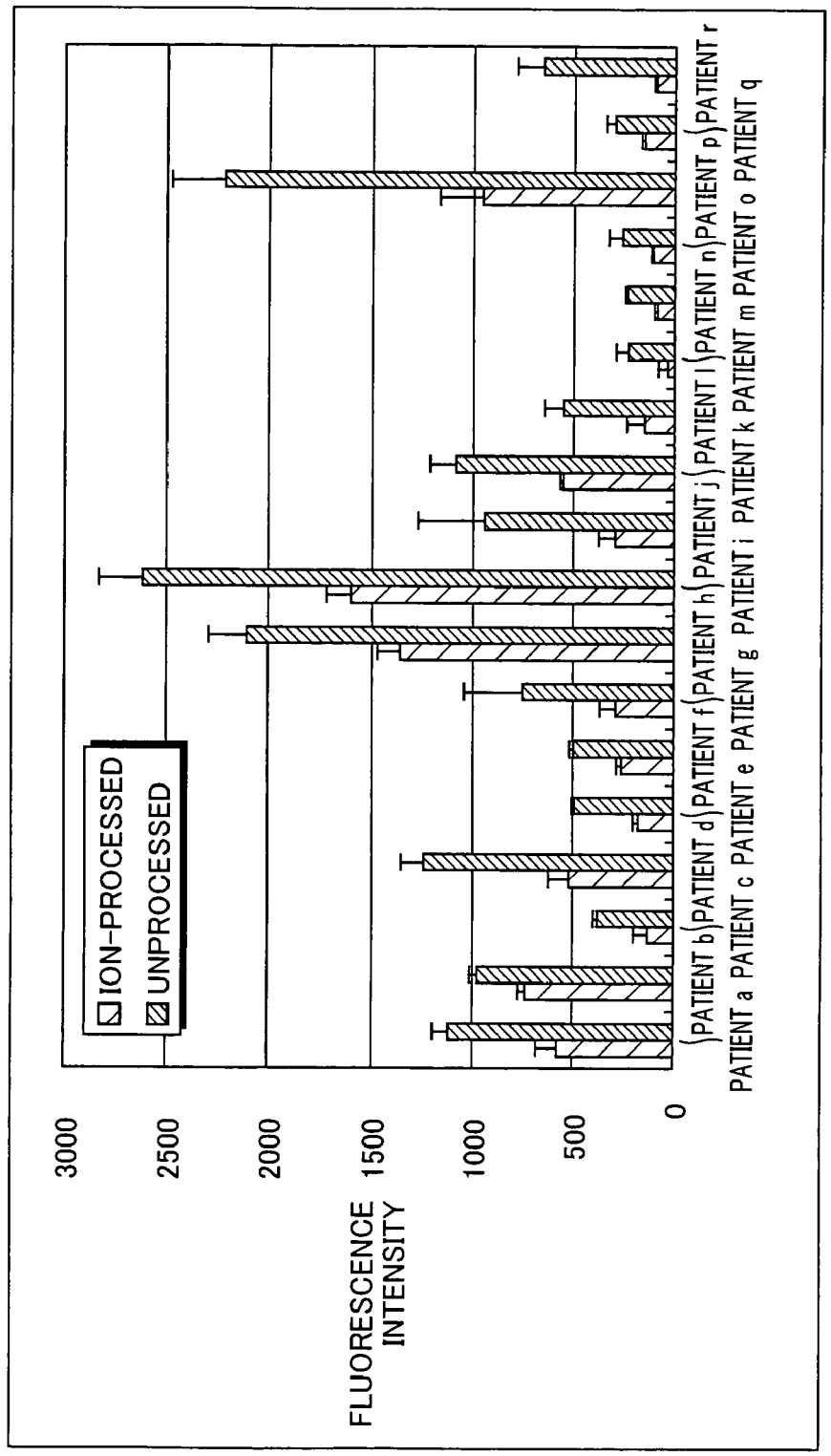
FIG. 10 represents relation of allergic reaction of serum IgE antibody and ion-processed and unprocessed antigenic substances (mite antigenic substance) of mite allergy patients a to r.

FIG. 9 is a schematic diagram of an apparatus for executing a method of deactivating antigenic substance by the function of positive and negative ions. FIG. 10 represents evaluation of reactivity between mite antigenic substance (referred to as Derf) and serum IgE of 18 patients a to r, by ELIZA method. The apparatus of FIG. 9 includes the ion generating device shown in FIG. 1 as in the apparatus of FIG. 3, and mass spectra of positive and negative ions emitted therefrom are as shown in FIGS. 2A and 2B, respectively.

<Apparatus for Executing the Method of Deactivating Antigenic Substance>

First, the apparatus shown in FIG. 9 used in this example is similar to that shown in FIG. 3 (and therefore, the same or corresponding portions are denoted by the same reference characters in FIGS. 3 and 9), except that equipment for reducing ozone is additionally provided. Specifically, in the apparatus shown in FIG. 9, one exhaustion outlet 1026 and nebulizer 1024 are connected with a filter 1029 interposed. Filter 1029 includes activated carbon and a molecular sieve, and has a function of removing ozone generated in the cylindrical sealed container 1027. Therefore, the ozone concentration in cylindrical sealed container 1027 is kept at 0.025 ppm or lower.

In the apparatus shown in FIG. 9, similar to the apparatus shown in FIG. 3, the antigenic substance 1038 is sprayed from inlet 1028 and falls naturally to recovery vessel 1025, while the substance is exposed to positive and negative ions and reacts therewith.

<Mite Dust and Antigenic Substance>

As the antigenic substance, antigenic substance extracted from mite dust was used. The mite dust was collected from ordinary household, captured from cushions and carpets by a vacuum cleaner with a mesh, and sifted thereafter. After collection, it was kept in a freezer at $-30°$ C.

In order to extract the antigenic substance from the mite dusts, 0.1 g of mite dust was stirred in 15 mL of 20 mM phosphate buffer solution (PBS, pH 7.4) for 16 hours at $4°$ C., and filtered through a membrane filter (0.2 μm), and the result was used as the mite antigenic substance. The mite antigenic substance includes Derf 1 and Derf 2, as antigenic substances.

<Protein Determination by Folin-Lowry Method>

A solution containing the mite antigenic substance, 0.2 ml, was mixed with 1 ml of solution D, as will be described later, and left for 10 minutes. Thereafter, solution A, as will be described later, was added by 0.1 ml and left for 30 minutes, and thereafter, light absorption was measured at 750 nm. Further, a standard series was formed with bovine serum albumin (BSA) to form a working curve, whereby the amount of protein in the mite antigenic substance was determined as BSA equivalent. As a result, protein concentration was 94.1 μg/ml. Reagents used here are as follows.

(Reagents)
Solution A; 1N of phenol reagent, as acid.
Solution B; 2% of $Na_2CO_3$+0.1 N of NaOH
Solution C, 0.5% of $CuSO_4.5H_2O$+1% of sodium citrate
Solution D; Solution B: Solution C=50:1 (v/v)

<Spraying and Recovery of Antigenic Substance>

The solution containing mite antigenic substance as the antigenic substance obtained in this manner (protein concentration 94.1 μg/ml) of 8 ml was put in a nebulizer 1024, which was connected to inlet 1028 of the apparatus shown in FIG. 9 for spraying antigenic substance solution. In order to recover the sprayed solution containing antigenic substance, recovery vessel 1025 was placed at the bottom of cylindrical sealed container 1027.

The nebulizer was connected to an air compressor and sprayed the antigenic substance 1038 through inlet 1028, using compressed air (flow rate 5 L/min). The amount sprayed was 8.0 ml (duration: 90 min). After 90 minutes, the antigenic substance sedimented at the bottom of cylindrical sealed container 1027 was recovered by recovery vessel 1025. It took about 90 seconds for the sprayed antigenic substance 1038 to naturally fall through cylindrical sealed container 1027.

Such spraying and recovery of antigenic substance was performed twice, with the ion generating device 1021 in operation (that is, with ion-processing) and not in operation (that is, without ion-processing).

When ion generating device 1021 was operated so that positive and negative ions reacted against the antigenic substance, the concentrations of positive and negative ions in the atmosphere (in cylindrical sealed container 1027) were measured by introducing air at the flow rate of 5 L/min by an air compressor through inlet 1028 of cylindrical sealed container 1027 for spraying antigenic substance solution, with ion generating devices 1021 mounted, and by placing air ion counter (part number ITC-201A) manufactured by Andes Denki at recovery vessel 1025 for recovering the antigenic substance solution, measuring the positive and negative ion concentrations. As a result, when voltage of 3.3 kV to 3.7 kV as the peak-to-peak voltage between electrodes was applied to ion generating devices 1021, the concentration of positive and negative ions was each 100,000/cm$^3$, in the cylindrical sealed container 1027. The atmosphere in the space had the temperature of $25°$ C. and relative humidity of 60% RH. As shown in FIGS. 2A and 2B, respectively, it was considered that the emitted positive ions were $H_3O^+$ $(H_2O)_n$ (n is 0 or a natural number) and negative ions were $O_2^-$ $(H_2O)_m$ (m is 0 or a natural number), and that these positive and negative ions generate hydrogen peroxide $H_2O_2$, hydrogen dioxide $HO_2$ or hydroxy radical .OH by the chemical reactions (1) and (2) described above.

<Reactivity Evaluation by ELISA Method>

Next, reactivity between the mite antigenic substance collected in this manner and the serum IgE antibody taken from mite allergy patients a to r was measured by ELISA (enzyme-liked immunosorbent assay) method. As for the antigenic substance, those reacted with positive and negative ions (ion-processed mite antigenic substance) and not reacted (unprocessed mite antigenic substance) were compared to evaluate the reactivity.

Specifically, using a 96-well plate for ELISA, ion-processed mite antigenic substance and unprocessed mite antigenic substance diluted to 0.1 μg/ml with bicarbonate buffer solution were applied, 50 μl per well. At the same time, human IgE standard double-diluted five times from 200 μg/ml with bicarbonate buffer solution was applied, 50 μl per well, and left still for 2 hours at a room temperature. The plate was washed three times with washing buffer, and a blocking buffer of 30011 was applied and left still overnight at $4°$ C.

After left still for one night, the plate washed three times, serum of mite allergy patient diluted 20 times with (3% of skim milk+1% of BSA)/PBST and incubated for one hour was applied, 50 μl per well, and left still for 4 hours. The plate washed three times, and biotin-labeled anti-human IgE diluted 1000 times with (3% of skim milk+1% of BSA)/PBST was applied, 50 μl per well, and left still for 2 hours.

After left still, the plate washed four times, 50 μl of alkali phosphatase labeled streptavidin diluted 1000 times with (3% of skim milk+1% of BSA)/PBST was applied, and left still for one hour at a room temperature. The plate washed five times, Attophos™ substrate buffer was applied, 50 μl per well, and left until colored, with light shielded. Fluorescent intensity was measured using a spectrophotometer (Cyto™ Fluor II). Results are as shown in FIG. 10.

As shown in FIG. 10, reactivity (binding characteristic) between serum IgE antibody of mite allergy patients and mite antigenic substance where the ion generating device 1021 was not operated (that is, positive and negative ions were not generated and ion-processing does not occur) and where concentrations of positive and negative ions were both 100,000/$cm^3$ was confirmed. All 18 mite allergy patients a to r exhibited significant decrease in reactivity between the ion-processed antigen and the serum IgE antibody of the patients (lower fluorescence intensity represents lower reactivity). Reagents used here are as follows.
(Reagents)
Sodium hydrogen carbonate buffer (bicarbonate buffer) solution; 100 mM of $NaHCO_3$ (pH 9.2~9.5)
Phosphate buffer solution (PBS); 4 g of NaCl, 0.1 g of $Na_2HPO_4.12H_2O$, 1.45 g of KCl, 1 g of $KH_2PO_4$, mixed with distilled water to 500 ml
PBST; PBS+0.5% of Tween-20
Blocking buffer solution; PBS+3% of skim milk+1% of BSA
Washing buffer solution; 43 g of $Na_2HPO_4.12H_2O$, 3.6 g of $NaH_2PO_4$, 263 g of NaCl, 15 ml of Tween-20, mixed with distilled water to 3 L.
<Ratio of Deactivation>

Using serum IgE of patients a to r described with reference to the ELIZA method above as the antibody, fluorescence intensities of unprocessed mite antigenic substance and ion-processed mite antigenic substance were found by the ELIZA method, and from the fluorescence intensities, the ratio of deactivation of allergic reaction was calculated in accordance with the following equation (3). The results are as shown in Table 3.

TABLE 3

| Patient | Ratio of Deactivation (%) |
|---|---|
| a | 48.8 |
| b | 24.8 |
| c | 67.2 |
| d | 58.2 |
| e | 64.2 |
| f | 48.3 |
| g | 61.7 |
| h | 35.4 |
| i | 38.9 |
| j | 69.1 |
| k | 49.2 |
| l | 73.2 |
| m | 84.2 |
| n | 63.7 |
| o | 59.7 |
| p | 57.0 |
| q | 50.0 |
| r | 86.5 |
| Average | 57.8 |

$$\text{Ratio of deactivation \%} = (1-E/F) \times 100 \quad (3)$$

E: Fluorescence intensity of ion-processed mite antigenic substance

F: Fluorescence intensity of unprocessed mite antigenic substance

As is apparent from Table 3, average ratio of deactivation among patients a to r was 57.8%, and therefore, it is expected that mite allergic disease could effectively be suppressed.

Example 3

In this example, deactivation of mite dust (antigenic substance contained therein) by the function of positive and negative ions was confirmed, directly using mite dust. Description will be given in the following with reference to FIGS. 11 to 13. Determination of protein mass in the mite antigenic substance included in mite dust by Folin-Lowry method was performed in the similar manner as in Example 2.
<Diffusion and Collection of Mite Dust>

Figure 11:
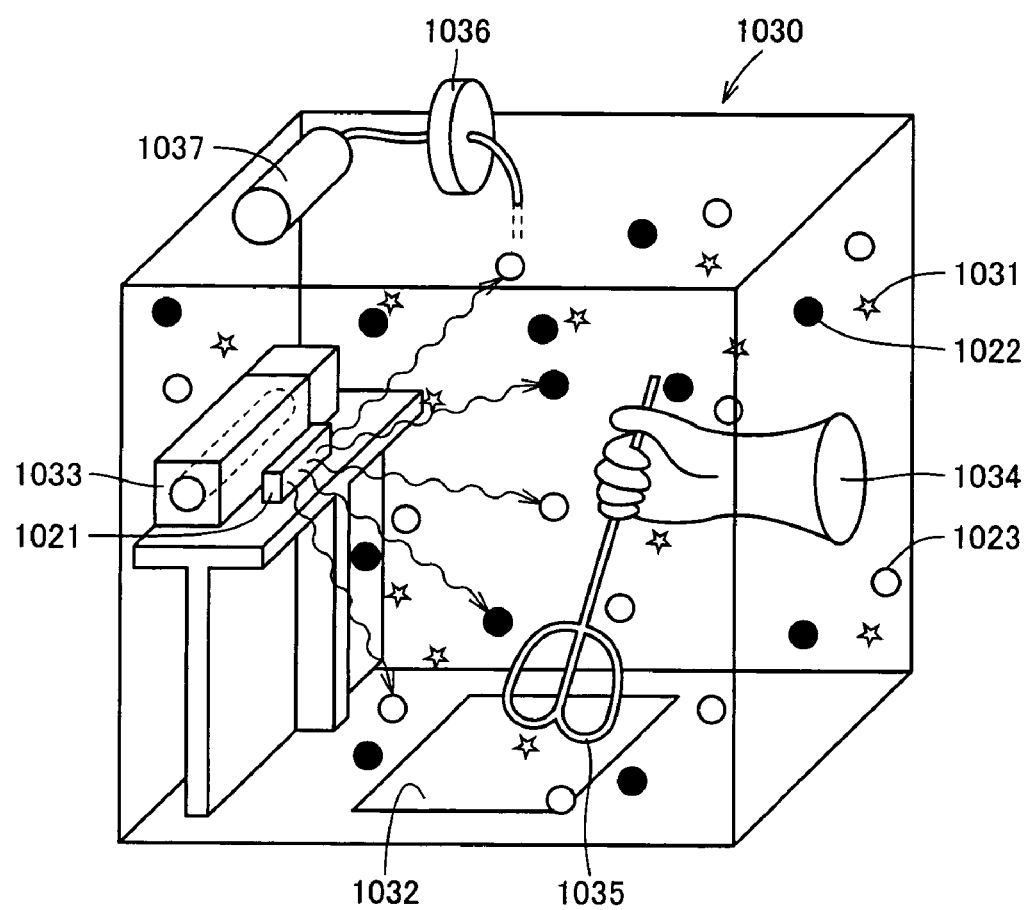
FIG. 11 is a schematic diagram showing an exemplary apparatus for executing the method of deactivating antigenic substance, including a blower and a recovery filter.

Mite dust was diffused and collected using an apparatus shown in FIG. 11 (in FIG. 11, portions denoted by the same reference characters as in other figures denote the same or corresponding portions). Specifically, the apparatus is formed of a sealed box 1030 having a blower 1033 and an operating window 1034, and at an air outlet of blower 1033, ion generating device 1021 is mounted.

First, both ion generating device 1021 and blower 1033 were operated. The operation condition was as follows: the peak-to-peak voltage between electrodes of ion generating device 1021 was adjusted to 90V so that the spatial average concentrations of positive and negative ions each attain 3000/$cm^3$, and fan flow rate of blower 1033 was set to 2 $m^3$/min.

The spatial average concentrations of both positive and negative ions in box 1030 were measured by measuring concentrations of positive and negative ions at five points apart from each other by at least 50 cm near the center of the box using air ion counter (part number ITC-201 A) manufactured by Andes Denki, and by calculating an average concentration among the five points, and the concentrations of the positive and negative ions were adjusted to attain 3000/$cm^3$ each. The atmosphere in the box had the temperature of 25° C. and relative humidity of 60% RH. As shown in FIGS. 2A and 2B, respectively, it was considered that the emitted positive ions were $H_3O^+$ $(H_2O)_n$ (n is 0 or a natural number) and negative ions were $O_2^-$ $(H_2O)_m$ (m is 0 or a natural number), and that these positive and negative ions generate hydrogen peroxide $H_2O_2$, hydrogen dioxide $HO_2$ or hydroxy radical .OH by the chemical reactions (1) and (2) described above.

Then, ion generating device 1021 and blower 1033 were stopped. Thereafter, an article 1032 carrying mite dust (2 g) was placed in box 1030, and ion generating device 1021 and blower 1033 were operated again, under the same condition as described above.

Thereafter, mite dust 1031 was diffused (scattered and caused to float) by flapping the article 1032 through a window 1034, using a diffuser 1035. The article 1032 may be a futon, blanket, carpet, tatami, pillow, cushion, pad or the like. In this example, a cushion was used. As the diffuser 1035, a flapper, a duster or a broom may be used. In this example, a flapper was used. As for the diffusing operation, the article 1032 may be swapped, shaken or dropped down. In this example, using a flapper as diffuser 1035, the cushion as article 1032 was flapped hard 20 times in 5 minutes.

Then, after flapping the cushion, an air suction pump 1037 mounted at an upper portion of box 1030 was operated, and the dust in box 1030 was sucked and collected for 30 minutes, using a recovery filter 1036.

After 30 minutes, air suction pump 1037 was stopped and, again, using a flapper as diffuser 1035, the cushion as article 1032 was flapped hard 20 times in 5 minutes. Then, air suction pump 1037 was again operated, and the dust in box 1030 was sucked and collected for 30 minutes, using a recovery filter 1036.

The amount of dust collected by recovery filter 1036 by two times of suction and collection described above was 0.7 mg.

For the operations described above, ion generating device 1021 was operated so as to cause reaction of positive and negative ions against mite dust (the mite dust processed in this manner will be referred to as ion-processed mite dust, and extraction therefrom will be referred to as ion-processed mite antigenic substance). For comparison, mite dust was collected in the same manner as described above, except that ion generating device 1021 was not operated (the sample for comparison will be referred to as unprocessed mite dust, and extraction therefrom will be referred to as unprocessed mite antigenic substance).

Figure 12:
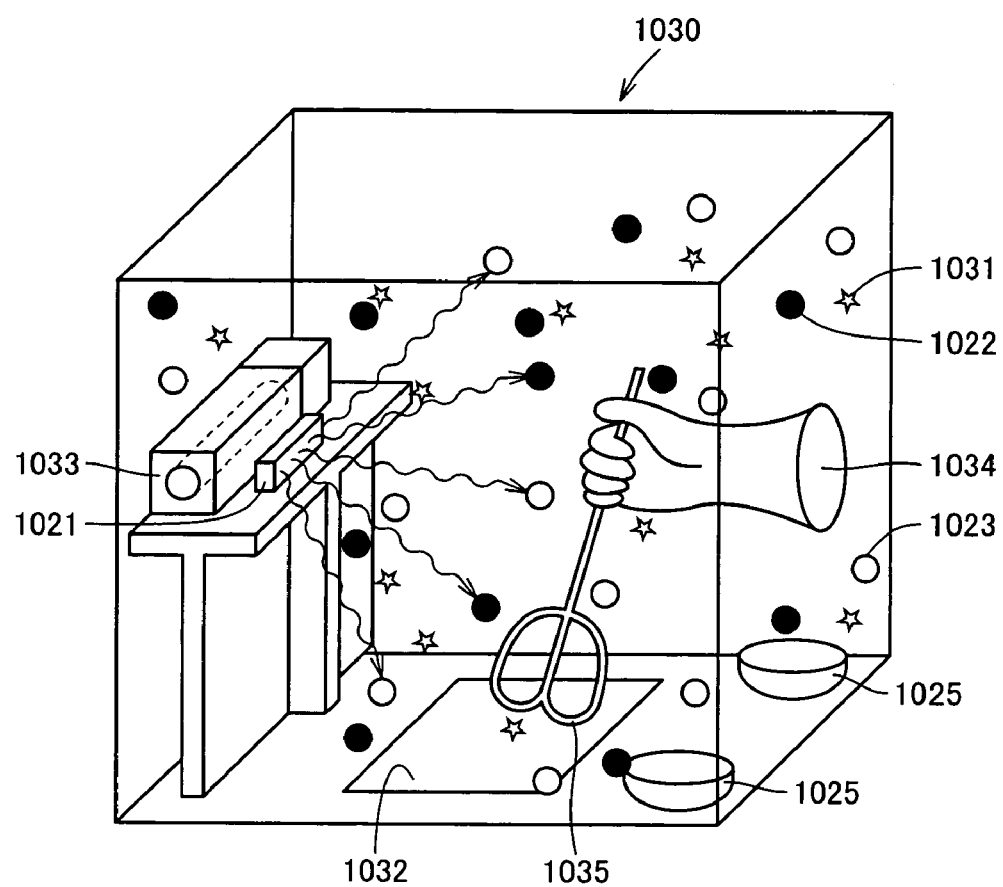
FIG. 12 is a schematic diagram showing an exemplary apparatus for executing the method of deactivating an antigenic substance, including a blower and a recovery vessel.

For such operation, various apparatuses other than the apparatus shown in FIG. 11 described above may be used. For example, in place of air suction pump 1037 and recovery filter 1036 of FIG. 11, a recovery vessel 1025 may be placed to collect dust that falls naturally, as shown in FIG. 12 (in which the same reference characters as FIG. 11 denote the same or corresponding portions).

<Evaluation by ELIZA Inhibition Method>

For quantitative evaluation of reactivity between ion-processed and unprocessed mite antigenic substances and serum IgE of mite allergy patients, ELIZA inhibition (enzyme-liked immunosorbent assay inhibition) method was used.

Specifically, mite antigenic substance was extracted from the diffused and collected mite dust, put in a centrifugal separator (Centriprep YM-10), and subjected to centrifugal condensation at 2500 rpm. Further, the condensation was put in a centrifugal separator (ULTRA FLEE-MC) and subjected to centrifugal condensation at 7000 rpm. Condensed ion-processed mite antigenic substance and condensed unprocessed mite antigenic substance were 5-times diluted from protein concentration of 7.66 µg/ml for 11 times. The diluted antigenic substances, 50 µeach, were mixed with 50 µl of 10-times diluted serum IgE of each patient, and pre-incubated overnight at 4° C.

Specifically, using a 96-well plate for ELISA, 50 µl of mite antigenic substance (not even sprayed) diluted to 1 µg/ml with bicarbonate buffer solution was applied to a well, and left still for 2 hours. The plate washed three times with washing buffer solution, and then, 300 µl of blocking buffer solution was applied and left still overnight at 4° C.

After left still overnight, the plate washed three times, and pre-incubated samples were applied, 50 µl per well, and left still for 4 hours. The plate washed three times, and biotin-labeled anti-human IgE diluted 1000 times with (3% of skim milk+1% of BSA)/PBST was applied, 50 µl per well, and left still for 2.5 hours.

After left still, the plate washed four times, 50 µl of alkali phosphatase labeled streptavidin diluted 1000 times with (3% of skim milk+1% of BSA)/PBST was applied, and left still for 1.5 hours at a room temperature. The plate washed five times, Attophos™ substrate buffer was applied, 50 µl per well, and left until colored, with light shielded. Fluorescent intensity was measured using a spectrophotometer (Cyto™ FluorII). The reagents used were the same as those listed above, unless specified differently.

Reactivity (binding characteristic) to the serum IgE antibody of mite allergy patients, where ion generating device was not operated (that is, reactivity to unprocessed mite antigenic substance) and where the device was operated to attain spatial average concentration of 3,000/cm$^3$ for each of positive and negative ions (that is, reactivity to ion-processed mite antigenic substance) was studied. The results are as shown in FIG. 13.

Figure 13:
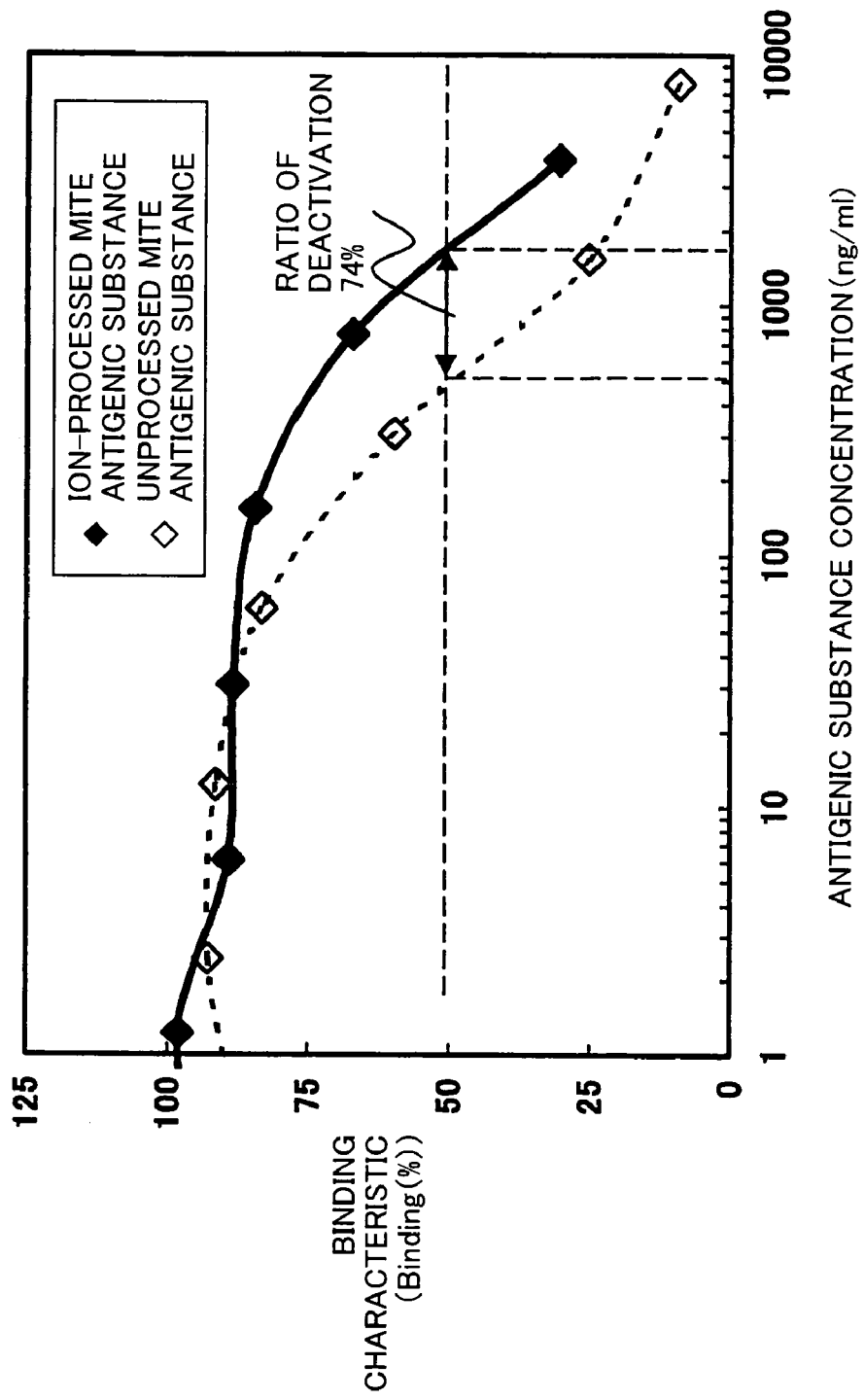
FIG. 13 represents relation of allergic reaction between the antigenic substance and the serum IgE antibody of mite allergy patients, when the mite dust was ion-processed and unprocessed, by ELISA inhibition method, with the spatial average concentration of positive/negative ions of 3000/cm$^3$.

As shown in FIG. 13, the amount of mite antigenic substance necessary for 50% inhibition (to lower reactivity of mite antigenic substance to serum IgE antibody to 50%) was 500 ng/ml in the case of unprocessed mite antigenic substance, while the necessary amount for 50% inhibition was 1900 ng/ml in the case of ion-processed mite antigenic substance, and therefore, the ratio of deactivation was confirmed to be 74%. Here, the ratio of deactivation was calculated in accordance with an equation similar to equation (1) above.

In this manner, it was confirmed that the positive and negative ions act directly on the antigenic substance and, in addition, act on the mite dust containing the antigenic substance. Further, the effect was confirmed that when spatial average concentration of positive and negative ions each attain 3000/cm$^3$, the antigenic substance could be deactivated.

Example 4

Functions of the positive and negative ions on mite dust were confirmed in the similar manner as in Example 3, except that, different from Example 3, the spatial average concentration of positive and negative ions each were set to 10,000/cm$^3$ (by setting the peak-to-peak voltage between electrodes of ion generating device 1021 to 100V and setting fan flow rate of blower 1033 to 8 m$^3$/min). The results are as shown in FIG. 14.

Figure 14:
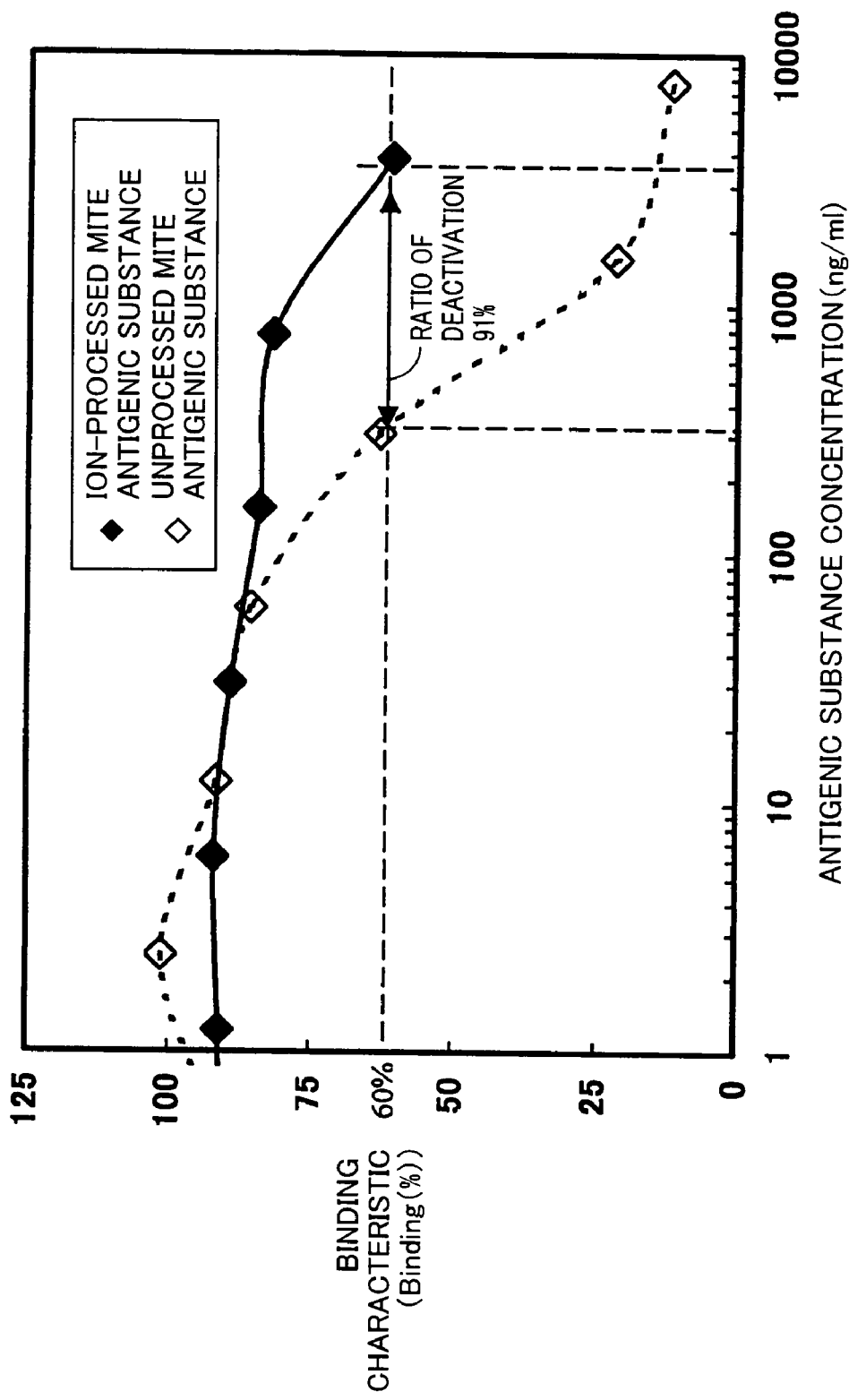
FIG. 14 represents relation of allergic reaction between the antigenic substance and the serum IgE antibody of mite allergy patients, when the mite dust was ion-processed and unprocessed, by ELISA inhibition method, with the spatial average concentration of positive/negative ions of 10000/cm$^3$.

As shown in FIG. 14, the amount of mite antigenic substance necessary for 60% inhibition (to lower reactivity of mite antigenic substance to serum IgE antibody to 60%) was 345 ng/ml in the case of unprocessed mite antigenic substance, while the necessary amount for 60% inhibition was 3823 ng/ml in the case of ion-processed mite antigenic substance, and therefore, the ratio of deactivation was confirmed to be 91%. Here, the ratio of deactivation was calculated in accordance with equation (1) as above.

In this manner, it was confirmed that when spatial average concentration of positive and negative ions each attain 10,000/cm$^3$, the antigenic substance could be deactivated.

When FIGS. 13 and 14 are compared, though there is a difference of 50% inhibition and 60% inhibition, it can be understood that the higher the spatial average concentration, the higher the ratio of deactivation, as the ratio of deactivation for 50% inhibition and 60% inhibition can be regarded substantially the same in accordance with FIG. 13.

As described above, by the method of the present invention, the antigenic substance can effectively be deactivated by the reaction with positive and negative ions. Thus, it is expected that the method can be used for effectively suppressing various allergic diseases such as hey fever and mite allergy, caused by such antigenic substances.

Further, by using the method or apparatus of the present invention inside or outside an air conditioning apparatus, it becomes possible to feed air with antigenic substance deactivated, or to directly deactivate the air-borne antigenic substance by ion emission described above.

In each of the above-described embodiments, description has been made mainly focusing on allergens included in pollen and mite. It is noted, however, that the air purifier in accordance with the present invention is also considered effective to allergens included in mold and the like, other than pollen and mite.

INDUSTRIAL APPLICABILITY

According to the method of the present invention, the antigenic substance can be deactivated by the function of positive and negative ions without necessitating the trouble of periodic filter exchange or the like and without any preventive difficulty such as individual difference in antibody development. Therefore, it is expected that the allergic disease can effectively be suppressed. Further, the positive and negative ions are introduced to react against the antigenic substance, without generating harmful ozone as a by-product. Further, by the apparatus of the present invention, the antigenic substance can be deactivated by emitting both positive and negative ions to the air.

Therefore, the air conditioning apparatus using the method or apparatus of the present invention can efficiently deactivate air-borne antigenic substance, and can provide comfortable living space that can suppress allergic disease.

The invention claimed is:

1. A method of deactivating an antigenic substance included in a living organism wherein said antigenic substance acts on a living body to cause an allergic reaction as one type of antigen-antibody reaction thereby inducing allergic disease, wherein the antigenic substance is a substance included in pollen of cedar, cypress or ragweed, or mites, which method comprises the step of:

causing positive and negative ions to act on said antigenic substance in an atmosphere in which each of positive ion concentration and negative ion concentration is at least about $50,000/cm^3$, wherein the positive ions are $H_3O^+(H_2O)_n$ (n is 0 or a natural number), and the negative ions are $O_2^-(H_2O)_m$ (m is 0 or a natural number).

2. The method of deactivating an antigenic substance according to claim 1, wherein the positive and negative ions are caused to act in an atmosphere in which each of positive ion concentration and negative ion concentration is at least about $100,000/cm^3$.

3. The method of deactivating an antigenic substance according to claim 1, wherein the positive and negative ions are caused to act where spatial average concentration of positive ions and spatial average concentration of negative ions are each at least about $3,000/cm^3$.

4. The method of deactivating an antigenic substance according to claim 1, wherein the positive and negative ions are caused to act where spatial average concentration of positive ions and spatial average concentration of negative ions are each at least about $10,000/cm^3$.

5. The method of deactivating an antigenic substance according to claim 1, wherein the positive and negative ions generate, by a chemical reaction, at least one of hydrogen peroxide ($H_2O_2$), hydrogen dioxide ($HO_2$) and hydroxy radical (.OH).

6. The method of deactivating an antigenic substance according to claim 1, wherein the antigenic substance is cedar antigenic substance.

7. The method of deactivating an antigenic substance according to claim 1, wherein the antigenic substance is mite antigenic substance or mite dust.

8. An apparatus for deactivating an antigenic substance included in a living organism wherein said antigenic substance acts on a living body to cause an allergic reaction as one type of antigen-antibody reaction thereby inducing allergic disease, wherein the antigenic substance is a substance included in pollen of cedar, cypress or ragweed, or mites, said apparatus having a mechanism for emitting positive and negative ions to the air, causing the positive and negative ions to act on the antigenic substance in an atmosphere in which each of positive ion concentration and negative ion concentration is at least about $50,000/cm^3$ and to generate at least one of hydrogen peroxide ($H_2O_2$), hydrogen dioxide ($HO_2$) and hydroxy radical (.OH).

9. The apparatus for deactivating an antigenic substance according to claim 8, emitting positive and negative ions to the air to provide an atmosphere in which each of positive ion concentration and negative ion concentration is at least about $100,000/cm^3$.

10. The apparatus for deactivating an antigenic substance according to claim 8, emitting positive and negative ions to the air to attain spatial average concentration of positive ions and spatial average concentration of negative ions each of at least about $3,000/cm^3$.

11. The apparatus for deactivating an antigenic substance according to claim 8, emitting positive and negative ions to the air to attain spatial average concentration of positive ions and spatial average concentration of negative ions each of at least about $10,000/cm^3$.

12. The apparatus for deactivating an antigenic substance according to claim 8, wherein the antigenic substance is cedar antigenic substance.

13. The apparatus for deactivating an antigenic substance according to claim 8, wherein the antigenic substance is mite antigenic substance or mite dust.

14. The apparatus for deactivating an antigenic substance according to claim 8, comprising an air conditioning mechanism.

* * * * *